(12) United States Patent
Johansson et al.

(10) Patent No.: US 9,381,166 B2
(45) Date of Patent: Jul. 5, 2016

(54) SYSTEMIC PRO-HEMOSTATIC EFFECT OF SYMPATHICOMIMETICS WITH AGONISTIC EFFECTS ON ALFA-ADRENERGIC AND/OR BETA-ADRENERGIC RECEPTORS OF THE SYMPATHETIC NERVOUS SYSTEM, RELATED TO IMPROVED CLOT STRENGTH

(75) Inventors: Pär Johansson, Dösjebro (SE); Niels H. Secher, Bagsværd (DK); Louise Bochsen, Lyngby (DK)

(73) Assignee: Rigshospitalet, Copenhagen (DK)

( * ) Notice: Subject to any disclaimer, the term of this patent is extended or adjusted under 35 U.S.C. 154(b) by 1586 days.

(21) Appl. No.: 12/681,352

(22) PCT Filed: Oct. 1, 2008

(86) PCT No.: PCT/DK2008/050242
§ 371 (c)(1),
(2), (4) Date: Sep. 2, 2010

(87) PCT Pub. No.: WO2009/043355
PCT Pub. Date: Apr. 9, 2009

(65) Prior Publication Data
US 2011/0201553 A1    Aug. 18, 2011

(30) Foreign Application Priority Data
Oct. 2, 2007   (DK) .................................. 2007 01418

(51) Int. Cl.
| | | |
|---|---|---|
| *A61K 31/00* | (2006.01) | |
| *A61K 31/137* | (2006.01) | |
| *A61K 33/14* | (2006.01) | |
| *G01N 33/86* | (2006.01) | |
| *G01N 33/94* | (2006.01) | |

(52) U.S. Cl.
CPC ............... *A61K 31/00* (2013.01); *A61K 31/137* (2013.01); *A61K 33/14* (2013.01); *G01N 33/86* (2013.01); *G01N 33/9433* (2013.01)

(58) Field of Classification Search
None
See application file for complete search history.

(56) References Cited

U.S. PATENT DOCUMENTS

| | | | | |
|---|---|---|---|---|
| 4,377,573 A * | 3/1983 | LeVeen | ............... | A61K 31/135 514/10.9 |
| 4,637,815 A | 1/1987 | Lemole | | |
| 4,665,095 A * | 5/1987 | Winn et al. | .................... | 514/401 |
| 2005/0075597 A1 | 4/2005 | Vournakis et al. | | |
| 2005/0261179 A1 | 11/2005 | Cuttitta et al. | | |
| 2007/0073210 A1 | 3/2007 | Hille et al. | | |
| 2008/0269347 A1 * | 10/2008 | Bruss et al. | .................... | 514/653 |
| 2013/0123298 A1 * | 5/2013 | Julia | ............... | 514/304 |

FOREIGN PATENT DOCUMENTS

| | | |
|---|---|---|
| EP | 0 248 150 A1 | 12/1987 |
| WO | WO97/04764 A1 | 2/1997 |
| WO | WO01/82937 A1 | 11/2001 |
| WO | WO2004/060172 A1 | 7/2004 |

OTHER PUBLICATIONS

Rickles, et al, 1976, The Effects of Epinephrine Infusion in Patients with Von Willebrand's Disease. J. Clin. Invest., 57: 1618-1625.*
Lo et al. Comparison of hemstatic effeicacy for epinephrine injection alone and injection combined with hemoclip therapy in treating high-risk bleeding ulcers. Gastrointestinal Endoscopy. 2006; 63(6): 767-773.*
Flordal et al. Hemostatic effects of ephedrine. Thrombosis Research. 1992; 68(3): 295-302.*
Rosch et al. Selective vasoconstrictor infusion in the management of arterio-capillary gastrointestinal hemmorrhage. Journal of Roentgenology. 1972; 116(2): 279-288.*
Durmus et al. Effect of dexmedetomidine on bleeding during tympanoplasty or septorhinoplasty. Journal of Anaesthesiology. 2007; 24:447-453.*
Henry et al. Effects of fibrinolytic inhibitors on mortality from upper gastrointestinal hemmorhage. British Medical Journal. 1989; 298:1142-1146.*
Br&A Reduction of blood loss during primary tangential excision with epinephrine infiltration .Ann. Medit. Burns Club Sep. 1995; vol. VIII-n.3, 1-6.*
Kawasaki et al. Do platelet activators (epinephrine, ADP, and collagen) affect whole blood clot formation on thromboelastogram? Anesthesiology. 2002; 96: Abstract No. A-534.*
Jennes et al. Effect of tranexamic acid on blood loss in burn surgery: a preliminary study. Journal of Burn Care and Research. Mar./Apr. 2003; 24; p. S59.*
Rickles et al. The effects of epinephrine infusion in patients with Von Willebrand's Disease. 57: 1618-1625, 1976).*
Westfall et al. (In: Brunton LL, Lazo JS, Parker KL, editors. Goodman & Gilman's: The pharmacological basis of therapeutics, 11th ed. New York, New York: McGraw-Hill; 2006. pp. 237-247).*
Br&A. Ann. Medit. Burns Club Sep. 1995; vol. VIII-n.3, 1-6.*
Kawasaki et al. Anesthesiology. 2002; 96: Abstract No. A-534.*
Jennes et al. Journal of Burn Care and Research. Mar./Apr. 2003; 24; p. S59.*
Banbury, M., et al. "Transfusion increases the risk of postoperative infection after cardiovascular Surgery," *J Am Coll Surg*. 202:131-138, Elsevier Inc., United States, (Jan. 2006).
Bassus, S., et al., "Platelet-dependent coagulation assays for factor VIII efficacy measurement after substitution therapy in patients with haemophilia A," *Platelets* 17:378-384, Informa Healthcare, United Kingdom, (Sep. 2006).
Beers, M.H. and Berkow, R., "The Merck Manual of Diagnosis and Therapy—Seventeeth Edition" 1999, Merck Research Laboratories, Whitehouse Station NJ, pp. 135-138.
Brace, L.D., "Qualitative platelet disorders," *Clin Lab Sci*. 20:48-55, ProQuest Science Journals, United States, (Winter 2007).
Butler, S., "Massive gastric hemorrhage and its treatment," *Med. Clin of North Amer*, W. B. Saunders Company, United States, (1953).
Cartotto, R., et al., "What are the acute cardiovascular effects of subcutaneous and topical epinephrine for hemostasis during burn surgery?," *Burn Care & Rehabilitation* 24: 297-305, American Burn Association, United States, (Sep./Oct. 2003).

(Continued)

*Primary Examiner* — Vanessa L Ford
*Assistant Examiner* — Sandra Dillahunt
(74) *Attorney, Agent, or Firm* — Dinsmore & Shohl LLP

(57) ABSTRACT

The present invention relates to a novel use and methods of treatment using sympathicomimetic agonists with pro-hemostatic activity.

4 Claims, 12 Drawing Sheets

(56) References Cited

OTHER PUBLICATIONS

Cheung, A., et al., "Comparison of treatment modalities for hemorrhagic shock," *Artif Cell Blood Substit Immobil Biotechnol.* 35:173-190, Informa Healthcare, United Kingdom, (Jan. 2007).
Chow, Y., et al., "Epinephrine promotes hemostasis in rats with cyclophosphamide-induced hemorrhagic cystitis," *Urology* 67: 636-641, Elsevier Inc., United States, (Sep. 2006).
Database Biosis, Kawasaki, J., et al., "Do Platelet Activators (Epinephrine, ADP and Collagen) Affect Whole Blood Clot Formation on Thromboelastogram?", 2 pages (2002).
Database Biosis, Kawasaki, J., et al., "Effects of Vasoactive Agents on the Whole Blood Clot Formation and Platelet Aggregation," 2 pages (2002).
Database WPI, Belichenko, I., et al., "Gastro:duodenal haemostasis treatment—involves endoscopic admin. of ethamsylate, adrenalin, gelatin and epsilon-amino-caproic acid mixt.," 1 page (1983).
Database WPI, Dovnar, I., et al., : "Haemostasis technique in haemorrhagic gastritis—by intravenous infusion of cimetidine and oral admin. of haemostatic mixt. contg. noradrenaline, barium sulfate and aluminum and magnesium hydroxide(s)," Thomson Scientific, London, 1 page (1994).
Database WPI, Ezhevskaya, A., et al., "Anesthethic aid method in surgically treating scoliosis cases," 1 page (2007).
Database WPI, Gerasimovich, E. et al., Thomson Scientific, London, 2 pages (1992).
Durmus, M., et al., "Effect of dexmedetomidine on bleeding during tympanoplasty or septorhinoplasty," *Eur J Anaesthesiology* 24:447-453, European Society of Anaesthesiology, Cambridge University Press, United Kingdom, (May 2007).
Elfellah, M., et al., "The relationship between the hypokalemic response to adrenaline, $\beta$-adrenoceptors, and $Na^+$-$K^+$ pumps in skeletal and cardiac muscle membranes in the rabbit," *J Cardiovascular Pharmacology* 15:62-67, Raven Press, United States, (Jan. 1990).
El-Sayed, M.S., "Effects of exercise on blood coagulation, fibrinolysis and platelet aggregation," *Sports Med* 22:282-298, Adis International Limited, New Zealand, (Nov. 1996).
Engoren, M., et al., "Effect of blood transfusion on long-term survival after cardiac operation," *Ann Thorac Surg.* 74:1180-1186, Elsevier Science Inc., United States, (Oct. 2002).
Fries, D., et al., "Efficacy of fibrinogen and prothrombin complex concentrate used to reverse dilutional coagulopathy—a porcine model," *Br J Anaesth.* 97:460-467, Board of Management of the British Journal of Anaesthesia, United Kingdom, (2006).
Gottumukkala, V.N., et al., "Assessing platelet and fibrinogen contribution to clot strength using modified thromboelastography in pregnant women," *Anesth Analg.* 89:1453-1455, International Anesthesia Research Society, United States, (Dec. 1999).
Hamilton, R., et al., "Phenylpropanolamine-associated intracranial hemorrhage in an infant," *Am J Emer Med* 18:343-345, W.B. Saunders Company, United States, (2000).
Hardy, J., et al., "The coagulopathy of massive transfusion," *Vox Sang* 89:123-127, Blackwell Publishing, United States, (Oct. 2005).
Hebert, P., et al., "A multicenter, randomized, controlled clinical trial of transfusion requirements in critical care," *Transfusion Requirements in Critical Care Investigators,* Canadian Critical Care Trials Group, *N Engl J Med.* 340:409-417, Massachusetts Medical Society, United States, (Feb. 1999).
International Search Report for International (PCT) Patent Application No. PCT/DK2008/050242, mailed Sep. 10, 2009, 10 pages.
Jakobsen, C., et al., "Effects of pre-operative metoprolol on cardiovascular and catecholamine response and bleeding during hysterectomy," *Eur J of Anaesthesiology* 9:209-215 (1992).
Jeschke, M., et al., "Blood transfusions are associated with increased risk for development of sepsis in severely burned pediatric patients," *Crit Care Med.* 35:579-583, Lippincott Williams & Wilkins, United States, (Feb. 2007).
Johansson, P.I., "The blood bank: from provider to partner in treatment of massively bleeding patients," *Transfusion* 47:176S-181S, Blackwell Publishing, United States, (Aug. 2007).
Kang, Y., "Thromboelastography in liver transplation," *Semin Thromb Hemost* 21:34-44, Thieme Medical Publishers, United States, (1995).
Karkouti, K., et al., "The independent association of massive blood loss with mortality in cardiac surgery," *Transfusion* 44:1453-1462, Blackwell Publishing, United States, (Oct. 2004).
Kawasaki, J., et al., "Electron microscopic evaluations of clot morphology during thrombelastography," *Anesth Analg* 99:1440-1444, International Anesthesia Research Society, United States, (Nov. 2004).
"Lactated Ringers's solution", http://en.wikipedia.org/wiki/Ringer%27s_Solution>, downloaded Aug. 6, 2009.
Lee, S., et al., "Traumatic Hemobilia: A complication of per cutaneous liver biopsy," *Gastroenterol.* 72: 941-944, Elsevier, United States, (May 1977).
Martini, W.Z., "The effects of hypothermia on fibrinogen metabolism and coagulation function in swine," *Metabolism Clin. Exp.* 56:214-21, Elsevier, United States, (Feb. 2007).
Martins, C., et al., "Effects of Dexmedetomidine on blood coagulation evaluated by Thromboelastography," *Revista Brasileira de Anestesiologia* 53: 705-719, (Nov./Dec. 2003).
McCrath, C., et al., "Thromboelastography maximum amplitude predicts postoperative thrombotic complications including myocardial infarction," *Anesth Analg.* 100:1576-1583, International Anesthesia Research Society, United States, (Jun. 2005).
Milasiene, V., et al., "TGF-$\beta$1 and TNF-$\alpha$after red blood cell transfusion colorectal cancer patients," *Exp Oncol.* 29:67-70, International Anesthesia Research Society, United States, (Mar. 2007).
Niemi, T., et al., "Gelatin and hydroxyethyl starch, but not albumin, impair hemostasis after cardiac surgery," *Anesth Analg* 102:998-1006, International Anesthesia Research Society, United States, (Apr. 2006).
Obika, L., "Cardiovascular and catecholamine responses to acute haemorrhage in anaesthetized potassium-adapted rats," *Res Exp Med* 193:175-185, Springer-Verlag, Germany, (1993).
Otsuka, Y., "Dynamic equilibration of coagulability and fibrinolytic activity of blood: Effect of sympathetic agents and role of $\alpha$, $\beta$ receptors," *Nagoya Medical J* 18: 321-346, Nagoya University School of Medicine, Japan, (1973).
Pluthero, F., et al., "Rapid assessment of platelet function using thromboelastography and small volumes of citrated whole blood," *Blood* 106:78B-79B, Am. Society of Hematology, United States, (2005).
Reed, W., et al., "Transfusion-associated microchimerism: a new complication of blood transfusions in severely injured patients," *Semin Hematol.* 44:24-31, Elsevier Inc., United States, (Jan. 2007).
Rivard, G., et al., "Evaluation of the profile of thrombin generation during the process of whole blood clotting as assessed by thrombelastography," *J Thromb Haemost.* 3:2039-2043, International Society on Thrombosis and Haemostasis, Blackwell Publishing Ltd., United Kingdom, (2005).
Roberts, H., et al., "A cell-based model of thrombin generation," *Semin Thromb Hemost.* 32:32-38, Thieme Medical Publishers, United States, (2006).
Rösch, J., et al., "Selective vasoconstrictor infusion in tihe management of arterio-capillary gastrointestinal hemorrhage", *Am J of Roentgenology, Radium Therapy & Nuclear Medicine,* Am Roentgen Ray Society, United States, 116: 279-288 (1972).
Salooja, N., & Perry, D.J. "Thrombelastography," *Blood Coagul Fibrinolysis* 12:327-337, Lippincott Williams & Wilkins, United States, (Jul. 2001).
Sharrock, N., et al., "Hypotensive epidural anesthesia for total hip arthorplastry," *Acta Orthopaedica Scandinavica,* 67: 91-107, Scandanavian University Press, Sweden, (1996).
Shore-Lesserson, L., et al., "Thromboelastography-guided transfusion algorithm reduces transfusions in complex cardiac surgery," *Anesth Analg* 88:312-319; International Anesthesia Research Society, United States, (Feb. 1999).
Simpson, P., "Perioperative blood loss and its reduction: The role of the anaesthetist," *Brit J Anaesthesia* 69: 498-507 (1992).
Singh, M., et al., "Plasma protein variations in hemophiliacs receiving factor replacement therapy," *Indian J Pediatr.* 74:459-462, Springer-Verlag, Germany, (May 2007).

(56) References Cited

OTHER PUBLICATIONS

Smith, J. E., "Effects of strenuous exercise on haemostasis," *Br J Sports Med* 37:433-435, group.bmj.com., United Kingdom, (2003).

Society of Thoracic Surgeons Blood Conservation Guideline Task Force, "Perioperative blood transfusion and blood conservation in cardiac surgery: The Society of Thoracic Surgeons and The Society of Cardiovascular Anesthesiologists Clinical Practice Guideline," *Ann. Thorac Surg* 83: S27-86, Elsevier Science Ltd, The Netherlands (2007).

Sørensen, B. and Ingerslev, J., "Tailoring haemostatic treatment to patient requirements—an update on monitoring haemostatic response using thrombelastography," *Haemophilia* 11:1-6, Blackwell Publishing Ltd., United Kingdom, (Nov. 2005).

Stainsby, D., et al., "Serious hazards of transfusion: a decade of hemovigilance in the UK," *Transfus Med Rev.* 20:273-282, Elsevier Inc., United States, (Oct. 2006).

Stocche, R., et al., "Intravenous clonidine in the induced arterial hypotension technique for tympanoplasty," *Revista Brasileira de Anestesiologia*, 53: 457-466, (Jul./Aug. 2003).

Teppo, H., et al., "Topical adrenaline in the control of intraoperative bleeding in adenoidectomy: a randomised, controlled trial," *Clin Otolaryngol.* 31:303-309, Blackwell Publishing Ltd., United Kingdom, (Aug. 2006).

Tomokiyo, K., et al., "A novel therapeutic approach combining human plasma-derived factors VIIa and X for haemophiliacs with inhibitors: evidence of a higher thrombin generation rate in vitro and more sustained hemostatic activity in vivo than obtained with factor VIIa alone," *Vox Sang.* 85:290-299, Blackwell Publishing Ltd., United Kingdom, (Nov. 2003).

Tongio, J., et al., "Control of massive hematuria after nephropyelotomy by selective intra-arterial injection of noradrenaline", *J de Radiologie*, 61: 135-136, Masson, France, (1980).

Vagianos, Q., et al., "Effect of intraarterial, intraportal or combined norepinephrine infusion on hemorrhage at experimental liver trauma in the rat," *European Surgical Research* 19:124-128, Karger AG, Switzerland (1987).

van Landeghem, Frank, K. H., et al., "Differential concentration-dependent effects of prolonged norepinephrine infusion on intraparenchymal hemorrhage and cortical contusion in brain-injured rats," *J. of Neurotrauma* 20:1327-1337 (Dec. 2003).

Vaslev, S.N., et al., "Massive transfusion exceeding 50 units of blood products in trauma patients," *J Trauma* 53:291-296, Lippincott Williams & Wilkins, United Kingdom, (Aug. 2002).

Velik-Salchner, C., et al., "The effect of fibrinogen concentrate on thrombocytopenia," *J Thromb Haemost.* 5:1019-1025, International Society on Thrombosis and Haemostasis, United States, (May 2007).

Welsby, I.J., et al., "The kaolin-activated thrombelastograph® predicts bleeding after cardiac surgery," *J Cardiothorac Vasc Anesth.* 20:531-535, United States, (Aug. 2006).

Zallen, G., et al., "Age of transfused blood is an independent risk factor for postinjury multiple organ failure," *Am J Surg.* 178:570-572, Excerpta Medica, Inc., United States, (Dec. 1999).

Anonymous: "Medication routes"; Ati Nursing Education, pp. 1-2; Retrieved online Sep. 18, 2015; URL:http://www.atetesting.com/ati_next_gen/skillsmodules/content/medication-administration-1/equipment/routes.html.

Chen, T. et al.; "Study in bleeding features of patients undergoing liver transplantation and evaluate the efficacy of rFVIIa"; *Modem Clinics in Surgery*, 5(2): 81-84, 2005.

Makwana, S. et al.; "Prefilled syringes: An innovation in parenteral packaging"; *Int J Pharm Investig.*, 200-206, 2011.

A concise explanation of the relevance of Chen et al., *Modern Clinics in Surgery*, 5(2): 81-84, 2005.

\* cited by examiner

SYSTEMIC PRO-HEMOSTATIC EFFECT OF SYMPATHICOMIMETICS WITH AGONISTIC EFFECTS ON ALFA-ADRENERGIC AND/OR BETA-ADRENERGIC RECEPTORS OF THE SYMPATHETIC NERVOUS SYSTEM, RELATED TO IMPROVED CLOT STRENGTH

This application is the National Stage of International Application Number PCT/DK2008/050242, filed Oct. 1, 2008, which claims the benefit of Danish Application No. PA 2007 01418, filed Oct. 2, 2007, both of which are incorporated by reference herein.

All patent and non-patent references cited in the application, or in the present application, are also hereby incorporated by reference in their entirety.

FIELD OF INVENTION

The present invention relates to a novel use and methods of treatment using sympathicomimetic agonists with pro-hemostatic activity.

BACKGROUND OF INVENTION

Blood coagulation is a process consisting of a complex interaction of various blood components (or factors) that eventually gives rise to a fibrin clot [Roberts et al. 2006]. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa). Initiation of the hemostatic process is mediated by the formation of a complex between tissue factor, exposed as a result of injury to the vessel wall, and Factor VIIa [Roberts et al. 2006]. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

It is often desirable to stimulate or improve the coagulation competence in a subject to control bleeding disorders that have several causes such as clotting factor deficiencies (e.g. hemophilia A and B or deficiency of coagulation Factors XI or VII) or clotting factor inhibitors [Singh et al. 2007] and also to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease [Brace 2007]. Bleeding is also a major problem in connection with surgery and other forms of tissue damage [Vaslev et al. 2002, Hardy et al. 2005].

In order to control the bleeding for example in connection with surgery or trauma a multifaceted treatment of the bleeding is initiated, including the below examples of treatments which are performed either alone or in combination:

1. Surgical hemostatic techniques by diathermia, clamping, sutures or packaging,
2. Administration of blood products such as red blood cells (RBC), plasma, containing coagulation factors and platelets,
3. Endovascular treatment (coiling),
4. Local hemostatic compounds including fibrin glue, pads with thrombin and other coagulation factors, local injection of vasoconstrictors,
5. Pro-hemostatic pharmaceuticals such as recombinant factor VIIa, recombinant factor XIIIa, and factor concentrates either produced from human plasma or by recombinant technique for FVIII and FIX,
6. Antifibrinolytic pharmaceuticals such as aprotinin, tranexamic acid and others [Cheung et al. 2007].

Pivotal for many of these medical treatments and procedures are the administration of allogenic blood products [Ferraris et al. 2007]. However, administration of allogenic blood products is associated with development of transfusion related complications such as:

a) intravascular hemolytic transfusion reaction,
b) delayed hemolytic transfusion reaction,
c) transfusion related acute lung injury (TRALI),
d) transfusion transmitted infections by virus (HTLV, HIV 1, 2, Hepatitis B, C, CMV) or bacteria,
e) transfusion associated graft versus host reaction (TA-GVHD),
f) posttransfusions purpura (PTP) [Stainsby et al. 2006].

In addition, transfusion of allogenic blood products is also associated with immunomodulation and immunosuppression predisposing for the development of postoperative infections as reported in orthopedic, burn and colorectal surgery [Banbury et al. 2006, Jeschke et al. 2007, Milasiene et al. 2007]. Furthermore, it has been reported by several groups that administration of blood products is independently associated with an increase in development of multiorgan failure [Zallen et al 1999] and mortality [Herbert et al. 1999, Engoren et al. 2002, Karkouti et al. 2004]. In fact, administration of red blood cells to patients undergoing surgical revascularization of coronary arteries dose-dependently is associated with increased 5 year mortality [Engoren et al. 2002]. In addition, transfusion of blood products may result in microchimerism with the immunocompetent donor leukocytes surviving indefinitely in the recipient [Reed et al. 2007].

Accordingly, in treatment of bleeding episodes, e.g. due to trauma, surgery or other medical treatments, the above-mentioned hazards of allogenic blood transfusion and the increasing shortage of allogenic blood donors and hence shortage of blood products calls for new options for pro-hemostatic treatments that improve the subjects clotting ability and hence reduce the bleeding and the need for allogenic blood transfusion in these subjects, without compromising the safety of the recipient.

In order to reduce blood loss locally, vasoconstrictors such as adrenaline and noradrenaline have been used either alone or in combination with any of the above-mentioned treatment alternatives. By local administration of vasoconstrictors the peripheral blood vessels are constricted whereby blood loss is reduced. By local administration, the systemic effects normally associated with vasoconstrictors are avoided, such as, for example, elevated systemic blood pressure and thus increased blood loss through open vessels.

Several reports exist on the use of vasoconstrictors as local hemostatic agents. For example in US 2007/0073210 is disclosed a wound dressing comprising a vasoconstrictive medicinal substance, such as adrenaline, as a ready to use product for local treatment of bleeding wounds.

Local administration of vasoconstrictors, such as adrenaline and noradrenaline, to a hemodialysis site in order to reduce complications associated with hemodialysis therapy is disclosed in US20050075597.

In WO0182937 compositions of intermacromolecular complexes such as, e.g. polyether, polyacids and polyalkylene and methods for making and using such compositions in reducing post-surgical bleeding is described. The application further describes the incorporation of vasoconstrictors in these compositions in order to have a local drug delivery at a surgical site.

Furthermore, the use of vasoconstrictors in a method to control gastrointestinal bleeding when injected directly into the peritoneal cavity or intragastrically is described U.S. Pat. No. 4,337,573. By this method, a local effect is obtained without any unwanted systemic effects because the vasoconstrictors are absorbed into the portal system and inactivated before entering systemic circulation.

In all these cited reports use is made of the vasoconstrictor effects of e.g. adrenaline and noradrenaline on the peripheral blood vessels by local administration in order to reduce bleeding.

SUMMARY OF INVENTION

The inventors of the present invention have surprisingly found that systemic administration of sympathicomimetic agonists such as adrenaline and noradrenaline in low doses (100 to a 1000 times lower than in the current indications i.e. cardiac arrest, anaphylactic shock) will result in a systemic activation of the coagulation system, while at the same time avoiding the side effects such as elevated blood pressure, and thus increased blood loss through open vessels, that would counteract the benefits of the treatment. By administration of low doses of systemic sympathicomimetic agonists a faster and stronger thrombin generation will take place, which will result in faster clot formation, a stronger and more durable clot, which is more resistant to shear and fibrinolytic enzymes. As a consequence of this, the systemic treatment with sympathicomimetic agonists such as adrenaline, noradrenaline, dopamine, dobutamine and ephedrine etc. in low doses are contemplated to reduce bleeding and/or risk of bleeding.

As will be described in further detail in the below, the inventors envisage that any sympathicomimetic substance, including adrenaline and noradrenaline, can be used in the present invention.

Thus, one object of the present invention relates to a previously unrecognized effect of sympathicomimetic agonists having pro-hemostatic activity related to improved clot strength when administered systemically by way of intravenous, intramuscular or subcutaneous, intrapulmonary, intraalveolarly, oral, sublingual, mucosal, or rectal routes as well as any nucleic acid constructs encoding such agonists, vectors and host cells comprising and expressing the nucleic acid, pharmaceutical compositions, uses and methods of treatment.

The present invention relates to novel uses and methods of treatment using sympathicomimetic agonists with pro-hemostatic activity resulting in improved clot strength, as well as nucleic acid constructs encoding such sympathicomimetic agonists, vectors and host cells comprising and expressing the nucleic acid and pharmaceutical compositions.

Thus an object of the present invention relates to an adrenergic receptor agonist for systemic administration for the treatment and/or prophylaxis of bleeding in a subject.

Another object of the present invention relates to novel uses and methods of treatment using sympathicomimetic agonists with pro-hemostatic activity in combination with compounds capable of blocking or minimizing any adverse effects that may be elicited by administration of the sympathicomimetic agonists. Such inhibitory compounds include blockers of the adrenergic receptors and specifically blockers of the beta subtype of the adrenergic receptors.

Another object of the present invention thus relates to a composition comprising an adrenergic receptor agonist and a beta blocker for the treatment or prophylaxis of bleeding in a subject.

A third object of the present invention relates to novel uses and methods of treatment using sympathicomimetic agonists with pro-hemostatic activity in combination with potassium in order to maintain serum potassium concentrations upon administration of the sympathicomimetic agonists alone or in combination with the adrenergic receptor blockers.

A third object of the present invention thus relates to a composition comprising an adrenergic receptor agonist, potassium in a pharmaceutically acceptable form and optionally a beta blocker for the treatment or prophylaxis of bleeding in a subject.

Additional aspects of the present invention and particular embodiments will be apparent from the description below as well from the appended claims.

DETAILED DESCRIPTION OF THE INVENTION

Figure 1:
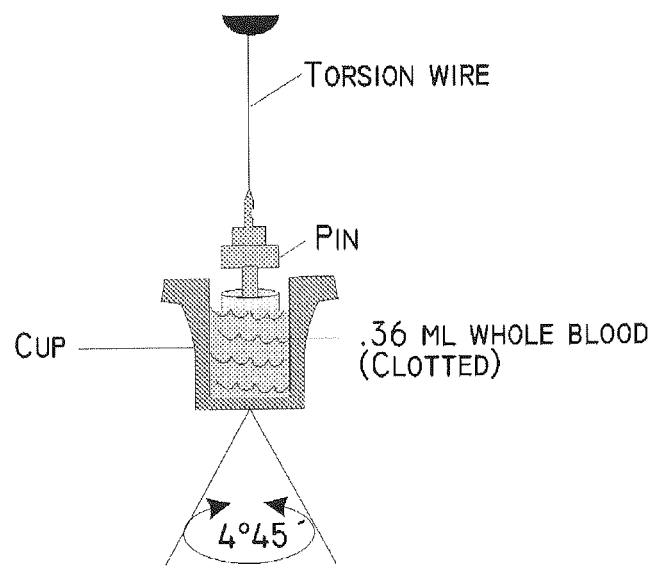
FIG. 1: TEG technology.

It has for many years been known that endogenous sympathetic activation secondary to a stress response results in an increase in procoagulant factors, platelet activation as well as in markers of increased fibrinolysis [Cannon et al. 1914]. Extensive research in athletes have corroborated that physical exercise results in increased levels of circulating sympathetic transmitters and that this is associated with an increased level of activated coagulation factors as well as increased fibrinolysis [Colman et al. 2001].

As mentioned above, sympathicomimetic agonists have been used for a considerable time as a local hemostatic agents due to their well-known vasoconstricting effects on the vasculature whereby bleeding can be reduced through contraction of the peripheral blood vessels.

Due to the effect of these sympathicomimetic agonists on heart rate, blood pressure, anxiety and redistribution of blood flow, no attempts have, to the inventors knowledge, been performed to stop or prevent bleeding episodes by systemic administration, because at the recommended doses the agonists will cause increased heart rate and blood pressure levels, anxiety and ventricular arrhythmia which together with the increased blood loss through open vessels is unacceptable in the majority of patients.

The inventors of the present invention have surprisingly found that the sympathicomimetic agonists activate the hemostatic system and improve clot strength and stability. By systemic administration of low doses (100 to a 1000 times lower than current indications) of sympathicomimetic agonists no significant elevation of the blood pressure is experienced and thereby blood loss due to this effect is absent, whereas the pro-hemostatic effect on the coagulation system prevails. Besides adrenaline, administration of e.g. other sympathicomimetic agonists such as noradrenaline, dopamine, dobutamine, ephedrine etc. (see herein below) is contemplated to lead to a systemic activation of the coagulation system, and importantly, to an improved hemostatic ability in humans due to improved clot strength. The mechanical strength of the clot is the determining factor for whether hemostasis can be achieved, since the strength of the clot determines if it can resist the shear forces of the flowing blood [Kawasaki et al 2004, Fries et al. 2006, Velik-Salchner et al. 2007, Bassus et al. 2006, Sørensen et al. 2005, Tomokiyo et al. 2003].

Interestingly, despite the speed, strength and durability of the clot formation, thrombosis does not occur more frequently with the agents of the present invention than without administration of the agents. This may in part be due to the fact that the sympathicomimetic agonists such as adrenaline and noradrenaline quickly, as in within minutes, are cleared from the body. Thus, the effects of the sympathicomimetic agonists are halted within minutes of termination of administration, and the hemostatic equilibrium of the particular subject is returned to its usual level. Furthermore, the clot is not after formation a permanent feature, the equilibrium between coagulation and fibrinolysis is changed, due to the increased speed of formation and longer durability of the clot following adrenaline administration, but there still is equilibrium between coagulation and fibrinolysis.

The advantages of the present invention are several fold: for the individual subject treated less blood is lost and thus less, if any, blood and/or blood products need be administered. Thus is beneficial to the subject as a reduced blood loss lessens the stress on the bodily systems of the subject and adverse effects known to medical practitioners and others skilled in the art that may follow from receiving blood and/or blood products are avoided and/or minimized. Obviously, with no or only a fraction of the blood/blood products used for a given procedure, money is saved and thus the administration of sympathicomimetic agonists has an economic incentive as well.

The term "activity" is intended to mean the ability to generate a clot of improved stability as well as an increased initiation, amplification and propagation of the hemostatic system, resulting in a faster formation of a clot of greater mechanical strength and stability together with increased resistance to fibrinolysis as compared to when the agonists are not administered.

The clinical importance of clot strength for hemostasis has further been illustrated in postoperative patients with ongoing bleedings, where a normalization of clot strength was associated with achievement of hemostasis [Johansson P I. 2007]. Patients with reduced clot strength, as evidenced by a reduced TEG MA (TEG: thrombelastography, MA: maximal amplitude), where treated with infusion of platelets until a normalization of clot strength, i.e. TEG MA was found, correlating with achievement of hemostasis. See Example 1 for a review of the TEG technology.

It is therefore envisaged that systemic administration of sympathicomimetic agonists, will be useful for treatment or prophylaxis of controlled or uncontrolled bleeding episodes in connection with various forms of e.g. trauma, surgery, post partum or due to congenital or acquired bleeding conditions.

Administration of the sympathicomimetic agonists of the present invention increases clot strength and stability and may be used to increase the clot strength and stability in a subject with subnormal clot strength and stability or may be used to increase clot strength and stability in a subject with normal clot strength and stability to a higher degree of strength and stability. Thus, clot strength and stability is shifted to a more stable level following administration of sympathicomimetic agonists. Preferably, the clot strength and stability after administering the sympathicomimetic agonist(s) is kept within the normal range of clot strength and stability but is either lifted from a subnormal level to within the normal range of clot strength and stability or is lifted from within the normal range of clot strength and stability towards the upper end of the normal range of clot stability. By staying within the normal range of clot strength and stability possible adverse effects are not encountered. Thus it is an object of the present invention that the clot strength and/or stability by administration of a sympathicomimetic agonist is shifted to the upper end of the normal range(s) of clot strength and/or stability.

The clot strength and stability and changes herein may be measured as increases in relative clot strength by the TEG (Thrombelastography) measurable parameter MA and clot stability by the TEG derivable parameter Lysis AUC. The maximal amplitude (MA) parameter reflects maximal clot strength i.e. the maximal elastic modus of the clot. The area under the lysis curve, i.e. area under the curve from MA is obtained (Lysis AUC) reflects degree of fibrinolysis (see FIG. 2). Both clot strength and stability may be measured, or one parameter only may be followed during a procedure such as either the clot stability or the clot strength. It is an object of the present invention that the clot strength measured by the MA increases relative to the MA prior to administration of a sympathicomimetic agonist by 105%, such as by 110%, such as by 115%, such as by 120%, such as by 125%, such as by 130%, such as by 135%, such as by 140%, such as by 145%, such as by 150%, such as by 155%, such as by 160%, such as by 165%, such as by 170%, such as by 175%, such as by 180%, such as by 185%, such as by 190%, such as by 195%, such as by 200% or more. Likewise it is an object of the present invention that the clot stability increases Lysis AUC. This parameter may with a TEG analysis be measured e.g. after addition of tissue plasminogen activator (tPA), and thus it is an object of the present invention that the clot stability measured by the Lysis AUC increases relative to the Lysis AUC prior to administration of a sympathicomimetic agonist by 105%, such as by 110%, such as by 115%, such as by 120%, such as by 125%, such as by 130%, such as by 135%, such as by 140%, such as by 145%, such as by 150%, such as by 155%, such as by 160%, such as by 165%, such as by 170%, such as by 175%, such as by 180%, such as by 185%, such as by 190%, such as by 195%, such as by 200% or more.

As follows from the above, disregarding which level of strength or stability is achieved, once the administration of the sympathicomimetic agonist stops, the levels will return to their pre-administrative levels, due to the rapid break down/turn over of the sympathicomimetic agonist.

The term "bleeding disorder" used herein will reflect any defect, congenital, acquired or induced, of cellular or molecular origin that is manifested in bleedings. The term "bleeding episodes" or "bleeding" is meant to include any episode were bleeding of a magnitude necessitating administration of blood products may occur, including uncontrolled and excessive bleeding both in connection with surgery and other forms of tissue damage in a subject.

A "subject" or "patient" includes humans and other mammals, and thus the methods are applicable to both human therapy and veterinary applications, in particular to human therapy. The term "mammal" includes humans, non-human primates (e.g. baboons, orangutans, monkeys), mice, pigs, cows, goats, cats, rabbits, rats, guinea pigs, hamsters, horse, monkeys, sheep or other non-human mammal.

Treatment, as used in this application, is therefore intended to include both prevention of an expected bleeding, such as in surgery, and regulation of an already occurring bleeding, such as in trauma, with the purpose of inhibiting or minimizing the bleeding. Prophylactic administration of the variant according to the invention is thus included in the term "treatment".

Sympathicomimetic Agonists

As apparent from the above, the treatment with sympathicomimetic agonists according to the present invention comprises adrenaline, noradrenaline, dobutamin, ephedrine, dopamine etc, see herein below. However, it is envisaged that the "sympathicomimetics" or "sympathicomimetic agonists" as used interchangeable herein, includes any pharmaceutical compounds with the same or similar activity as noradrenaline (norepinephrine) and adrenaline (epinephrine). This group of compounds, having predominantly peripheral action, can be divided into:

Directly acting sympathicomimetics that acts by stimulating the receptors of the sympathetic nervous system, and Indirectly acting sympathicomimetics that act by either releasing transmitters from the prejunctional nerve ends or by inhibiting their removal from the synaptic junction.

Directly acting sympathicomimetics act upon the adrenergic receptors (adrenoceptors), these comprising the $\alpha_1$-, $\alpha_2$-, $\beta_1$, $\beta_2$- and $\beta_3$-subtypes [Goldstein. 2006]. Any sympathicomimetic agonist is of relevance for the present invention for use in the treatment and/or prophylaxis of bleeding in a subject. Such sympathicomimetic agonists include but are not limited to agonists that are ligands of any one or more of the abovementioned receptors. Some sympathicomimetic agonists are specific for one or more of the abovementioned receptors; for example a particular agonist may be alpha-1 specific, or be alpha specific indicating that the agonist will bind either of the two known alpha receptors, or may be an agonist capable of interacting with any of the adrenergic receptors; an example hereof is adrenaline. Examples of all of these types of sympathicomimetic of relevance to the present invention include, but are not limited to: Adrenaline (epinephrine), Noradrenaline (norepinephrine), Phenylephrine, Methoxamine, Cirazoline, Xylometazoline, Methylnorepinephrine, Oxymetazoline, Dexmedetomidine, Clonidine, Lofexidine, Xylazine, Tizanidine, Guanfacine, Guanabenz, Guanoxabenz, Guanethidine, Methyldopa, amidephrine, amitraz, anisodamine, apraclonidine, brimonidine, cirazoline, detomidine, dexmedetomidine, ergotamine, etilefrine, indanidine, lofexidine, medetomidine, mephentermine, metaraminol (e.g. Aramine), methoxamine, midodrine, mivazerol, naphazoline, norfenefrine, octopamine, oxymetazoline, phenylpropanolamine, rilmenidine, romifidine, synephrine, talipexole and tizanidine, Dopamine (e.g. Intropine) Dobutamine, Dobutrex, Isoproterenol, Salbutamol (Albuterol in USA), Bitolterol mesylate, Formoterol, Isoprenaline, Levalbuterol, Metaproterenol, Salmeterol, Terbutaline, Ritodrine, Fenoterol, Clenbuterol, L-796568, Amibegron, Solabegron, arbutamine, befunolol, bromoacetylalprenololmenthane, broxaterol, cimaterol, cirazoline, denopamine, dopexamine, etilefrine, hexoprenaline, higenamine, isoetharine, isoxsuprine, mabuterol, methoxyphenamine, nylidrin, oxyfedrine, pirbuterol, prenalterol, procaterol, ractopamine, reproterol, rimiterol, ritodrine, tretoquinol, tulobuterol, xamoterol, and zinterol. Brand names of these compounds may vary from company to company and country to country; aliases of the above-mentioned compounds or other sympathicomimetic agonists are included within the scope of the present invention.

Preferably, compounds of the present invention for administration for prevention and/or treatment of bleeding in a subject comprises agonists of the Alpha-1 adrenergic receptor, such as but not limited to: Adrenaline (epinephrine), Noradrenaline (norepinephrine), Phenylephrine, Methoxamine, Cirazoline, Xylometazoline Methylnorepinephrine, and Oxymetazoline; as well as Alpha-2 adrenergic receptor agonists such as, but not limited to: Adrenaline (epinephrine), Noradrenaline (norepinephrine), Dexmedetomidine, Clonidine, Lofexidine, Xylazine, Tizanidine, Guanfacine, Guanabenz, Guanoxabenz, Guanethidine, and Methyldopa; and agonists that interact with both alpha receptors (and in some instances also the beta receptors), examples of these including, but again not being limited to: amidephrine, amitraz, anisodamine, apraclonidine, brimonidine, cirazoline, detomidine, dexmedetomidine, epinephrine, ergotamine, etilefrine, indanidine, lofexidine, medetomidine, mephentermine, metaraminol, methoxamine, midodrine, mivazerol, naphazoline, norepinephrine, norfenefrine, octopamine, oxymetazoline, phenylpropanolamine, rilmenidine, romifidine, synephrine, talipexole and tizanidine.

Likewise, examples of sympathicomimetic agonists that according to the present invention may be administered for the prevention and/or treatment of bleeding in a subject are agonists that interact with the beta receptors, these include, but are not limited to agonists that bind the Beta 1 adrenergic receptor, such as, but not restricted to: Noradrenaline, Isoprenaline, Dobutamine, Dobutrex, and Isoproterenol (β1 and β2); the Beta-2 adrenergic receptor agonists, again including but not limited to: Salbutamol (Albuterol in USA), Bitolterol mesylate, Formoterol, Isoprenaline, Levalbuterol, Metaproterenol, Salmeterol, Terbutaline, Ritodrine, Fenoterol, Isoproterenol (β1 and β2), and Clenbuterol; as well as the following non-limiting examples of agonists that bind the Beta-3 adrenergic receptor: L-796568, Amibegron, Solabegron, Noradrenaline, adrenaline, and isoprenaline; and the sympathicomimetic agonists that may bind either of the beta receptors (and in some cases also the alpha receptors), that list including but not being restricted to: arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, pirbuterol, prenalterol, procaterol, ractopamine, reproterol, rimiterol, ritodrine, tretoquinol, tulobuterol, xamoterol, and zinterol.

Thus it is an object of the present invention to provide compounds, specifically agonists of the adrenergic receptors, herein also referred to as sympathicomimetic agonists for the prevention and/or treatment of bleeding in a subject; examples of such compounds are given in the above.

The agonistic substance may be any endogenous or exogenous agonistic substance affecting any one or more of the $\alpha_1$, $\alpha_2$, $\beta_1$, $\beta_2$, $\beta_3$ adrenergic receptors. Furthermore, the agonistic substance may comprise any human, non-human, recombinant or by any other means manufactured agonistic substance affecting any one or more of the $\beta_1$, $\alpha_2$, $\beta_1$, $\beta_2$, $\beta_3$ adrenergic receptors of the sympathetic nerve system.

Preferably, sympathicomimetic agonists for the prevention and/or treatment of bleeding in a subject include but are not limited to agonists capable of binding at least one adrenergic receptor subtype.

Most preferably the sympathicomimetic agonists for the prevention and/or treatment of bleeding in a subject include but are not limited to adrenaline, noradrenaline, dobutamin, dobutrex, and dopamine, as well as metabolic products and chemically related synthetic derivates hereof.

Thus, sympathicomimetic agonists may further include any agonist with an agonistic effect on α-adrenergic and/or β-adrenergic receptors, including any subtypes (e.g. $\alpha_1$-, $\alpha_2$-, $\beta_1$, $\beta_2$- and $\beta_3$-subtypes), of the sympathetic nervous system, such as but not limited to adrenaline, noradrenaline, dopamine, dobutamin, dobutrex, ephedrine and other known or yet undiscovered chemical or biological substances or compounds where any of the above mentioned are included.

The agonistic substance or derivatives hereof may also be in a combination of two or more, such as three or more, four or more and five or more of any of the sympathicomimetics agonist discussed above.

In a specific embodiment of the present invention, the sympathicomimetic agonists comprise adrenaline and/or noradrenaline and/or dobutamine. Analogs of these substances may also be useful in the present invention.

In a still further embodiment of the present invention, the sympathicomimetic agonist comprises or is adrenaline (epinephrine).

In a still further embodiment of the present invention, the sympathicomimetic agonist comprises or is noradrenaline (norepinephrine).

The terms adrenaline and epinephrine are used interchangeably herein and both denote the compound defined in formula I with IUPAC name: (R)-4-(1-hydroxy-2-(methylamino)ethyl)benzene-1,2-diol:

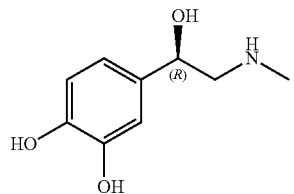

Formula I

Likewise, the terms noradrenaline and norepinephrine are used interchangeably herein and both denote the compound defined in formula II with IUPAC name: 4-(2-Amino-1-hydroxyethyl)benzene-1,2-diol:

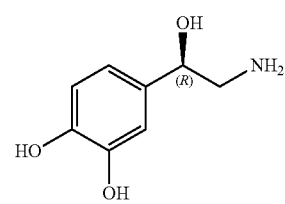

Formula II

Any sympathicomimetic able of inducing an activation of the hemostatic system equal to the 3 microgram/kg/hour of adrenaline is contemplated to induce a significant pro-hemostatic effect. Thus, a method for testing the hemostatic efficacy and/or the required dose of a sympathicomimetic agonist comprises the following steps:

a) administering to a subject and/or to a blood sample taken from a subject a sympathicomimetic agonist to be tested, b) conducting a TEG analysis on a blood sample from the subject, c) comparing the at least one measured parameter such as but not limited to: R value (clotting time), K value (clot kinetics), Angle or alpha (representing velocity of clot formation) MA, maximal amplitude, (the maximal physical clot strength), Lysis AUC (the area under the fibrinolysis curve AUC) and/or fibrinolysis time (LY) with the same one or more parameters following the administration of 3 microgram/kg/hour of adrenaline, wherein the parameters obtained for the 3 microgram/kg/ hour of adrenaline may be obtained from the same subject being tested with the sympathicomimetic agonist or a reference value/parameter obtained in advance.

By reference value is understood a value that has been obtained after repeated testing of the effects of administering 3 microgram/kg/hour of adrenaline to a statistically relevant number of subjects. The reference value may alternatively be based on the effects of administering another concentration of adrenaline, such as but not limited to: between 1 microgram/kg/hour of adrenaline and 10 microgram/kg/hour of adrenaline, dependent upon which effect is desired to be achieved by the sympathicomimetic agonist.

The method for testing the hemostatic efficacy and/or the required dose of a sympathicomimetic agonist may optionally comprise an additional step relating to from where the blood sample from the subject is collected, namely whether it is collected from an artery or a vein and dependent hereon, the sample(s) on which the reference value(s) is/are based must have been collected from the same arterial or venous source to ensure accuracy.

Thus, in one aspect of the present invention the blood sample to be analyzed and the sample or samples (such as those on which a reference value is based) with which it is compared are all drawn from arterial blood.

In another aspect of the present invention the blood sample to be analyzed and the sample or samples (such as those on which a reference value is based) with which it is compared are all drawn from venous blood.

Therefore it follows that the method for testing the hemostatic efficacy and/or the required dose of a sympathicomimetic agonist may further comprise the following steps:
  a) administering to a subject and/or to a venous or arterial blood sample taken from a subject a sympathicomimetic agonist to be tested,
  b) conducting a TEG analysis on a blood sample from the subject,
  c) comparing the at least one measured parameter such as but not limited to: R value (clotting time), K value (clot kinetics), Angle or alpha (representing velocity of clot formation) MA, maximal amplitude, (the maximal physical clot strength), Lysis AUC (the area under the fibrinolysis curve AUC) and/or fibrinolysis time (LY) with the same one or more parameters following the administration of 3 microgram/kg/hour of adrenaline as measured on a venous or arterial blood sample, the sample being drawn from the same source as in a) wherein the parameters obtained for the 3 microgram/kg/hour of adrenaline may be obtained from the same subject being tested with the sympathicomimetic agonist or a reference value/parameter obtained in advance.

By reference value is understood a value that has been obtained after repeated testing of the effects of administering 3 microgram/kg/hour of adrenaline to a statistically relevant number of subjects.

Preferably, a sympathicomimetic agonist of the present invention is a substance capable of altering one or more of the TEG measurable parameters of the blood of a subject to which the substance is administered such as: lowering the R value (clotting time), lowering the K value (clot kinetics), increasing the Angle or alpha (representing velocity of clot formation), and/or increasing the MA, maximal amplitude, (the maximal physical clot strength), increasing the Lysis AUC (the area under the fibrinolysis curve AUC) and/or increasing the fibrinolysis time (LY). Preferably, a sympathicomimetic agonist of the present invention is a substance capable of altering one or more of the TEG measurable parameters of the blood of a subject to which the substance is administered such as lowering the R value (clotting time), lowering the K value (clot kinetics), increasing the Angle or alpha (representing velocity of clot formation), and/or increasing the MA, maximal amplitude, (the maximal physical clot strength). Most preferably, a sympathicomimetic agonist of the present invention is a substance capable of altering all of the following TEG measurable parameters of the blood of a subject to which the substance is administered by lowering the R value (clotting time), lowering the K value (clot kinetics), and increasing the MA, maximal amplitude, (the maximal physical clot strength).

In this manner it has been found, that noradrenaline may be administered in the same dose interval as adrenaline, and dopamine at a dose of 10-100× higher (for example 30-300 microgram/kg/hour) than adrenaline and noradrenaline, and dobutamin may be administered at a dose of 10-100× higher (for example 30-300 microgram/kg/hour) than adrenaline and noradrenaline.

Beta Blockers

A current indication for which adrenaline is used is for the treatment cardiac arrest, anaphylactic shock and other cardiac dysrhythmias resulting in diminished or absent cardiac output. The action of adrenaline is to increase peripheral resistance via α1-adrenoceptor vasoconstriction, so that blood is shunted to the body's core, and the β1-adrenoceptor response which is increased cardiac rate and output (the speed and pronouncement of heart beats) resulting in amongst others: high blood pressure. The consequence of especially the beta-1 mediated response: increased cardiac rate, cardiac output and high blood pressure, is detrimental to subjects that are bleeding, as this will increase the rate with which blood is being pumped out of the body. Surprisingly, the inventors of the present invention have found, that administration of adrenaline at doses 100-1000 times lower than the doses administered for the treatment of cardiac arrest increases the hemostatic ability of the blood. If dysrhythmias, and especially tachycardia, never the less are sought prevented, an aspect of the present invention comprising the co-administration of a sympathicomimetic agonist with a beta-1 blocker accommodates this.

For example, adrenaline and other sympathicomimetic agonists comprise the pro-hemostatic properties whereas the beta-1 blocker attenuates the agonist's effect on myocardial excitability, including development of tachycardia/tachyarrhythmia while preserving cardiac output as well as maintaining unaltered blood pressure. The combination of adrenaline or another sympathicomimetic agonist and a beta-1 receptor blocker enables an improved pro-hemostatic response than possible by adrenaline alone, due to blockade of the unwanted side effects of adrenaline as outlined above.

In order to avoid any possibility of increasing the subjects' blood pressure or inducing any other unwanted systemic or local reactions, an embodiment of the present invention relates to the administration of a sympathicomimetic agonist in combination with a compound capable of blocking the actions of the beta adrenergic receptors, i.e. a beta blocker for the prevention and/or treatment of bleeding in a subject.

Beta blockers (sometimes written as β-blocker) are a class of drugs well known to those skilled in the art that used for various indications, but particularly for the management of cardiac arrhythmias and cardioprotection after myocardial infarction (heart attack). Beta blockers inhibit these normal epinephrine-mediated sympathetic actions, but have minimal effect on resting subjects. That is, they reduce the effect of excitement/physical exertion on heart rate and force of contraction, dilation of blood vessels and opening of bronchi, and also reduce tremor and breakdown of glycogen. It is therefore expected that non-selective beta blockers have an antihypertensive effect. The antihypertensive mechanism appears to involve reduction in cardiac output (due to negative chronotropic and inotropic effects), reduction in renin release from the kidneys, and a central nervous system effect to reduce sympathetic activity (for those β-blockers that do cross the blood-brain barrier, e.g. Propranolol). Beta blockers are also known as beta-adrenergic blocking agents, beta-adrenergic antagonists, or beta antagonists.

As stated above, there are three known types of beta adrenergic receptors and any compound capable of blocking the action of one or more of these is of relevance to the present invention. Examples of beta blockers that may be used in combination with a sympathicomimetic agonist for the prevention and/or treatment of bleeding in a subject include, but are not limited to: Acebutolol, Alprenolol, Amosulalol, Arotinolol, Atenolol, Befunolol, Betaxolol, Bevantolol, Bisoprolol, Bopindolol, Bucindolol, Bunitrolol, Bupranolol, Butaxamine, Carazolol, Carteolol, Carvedilol, Celirolol, Esmolol (Brevibloc), Indenolol, Labetalol, Landiolol, Levobetaxolol, Levobunolol, Mepindolol, Metipranolol, Metoprolol (Seloken), Nadolol, Nebivolol, Nipradilol, Oxprenolol, Penbutolol, Pindolol, Propranolol, Sotalol, Talinolol, Tertalolol, Tilisolol, and Timolol and other known or yet undiscovered chemical or biological substances or compounds where any of the above mentioned are included. Brand names of these compounds may vary from company to company and country to country; aliases of the abovementioned compounds or other beta blockers are included within the scope of the present invention.

An aspect of the present invention relates to the administration of a sympathicomimetic agonist in combination with a beta blocker for the prevention and/or treatment of bleeding in a subject, the beta blocker being a non-selective agent (i.e. may bind or block the action of more than one beta adrenergic receptor), such as, but not restricted to: Alprenolol, Carteolol, Levobunolol, Mepindolol, Metipranolol, Nadolol, Oxprenolol, Penbutolol, Pindolol, Propranolol, Sotalol, and Timolol.

Another aspect of the present invention relates to the administration of a sympathicomimetic agonist in combination with a beta blocker for the prevention and/or treatment of bleeding in a subject, the beta blocker being a selective agent (i.e. an agent that binds to or block the action of a specific beta adrenergic receptor) such agents comprising but not being limited to: β1-Selective agents such as Acebutolol, Atenolol, Betaxolol, Bisoprolol, Esmolol, Metoprolol (Seloken), Nebivolol, Amosulalol, Landiolol, and Tilisolol; or β2-Selective agents such as Butaxamine; or beta 3 selective agents.

The most preferred beta blocker is a beta-1 receptor blocker with a high cardioselectivity (i.e. β1/β2 ratio) limiting the blockade to the beta-1 receptor. The manner of calculating the cardioselectivity of a compound is known to the person skilled in the art. Generally, it is the relationship between a given compounds affinity for the beta-1 and beta-2 receptor, with a high affinity for the beta-1 receptor (i.e. higher than the affinity for the beta-2 receptor) being preferred. Furthermore the chosen beta-1 receptor blocker has a T½ (half life) of 3-9 min enabling full blocker effect after administration of a loading dose for 1-3 min and likewise the effect is rapidly reversible after discontinuation. Thus the most preferred beta blocker to be used in combination with a sympathicomimetic agonist for the prevention and/or treatment of bleeding in a subject may be chosen from the β1 (beta 1)—Selective agents such as Acebutolol, Atenolol, Betaxolol, Bisoprolol, Esmolol, Metoprolol (Seloken), Nebivolol, Amosulalol, Landiolol, and Tilisolol.

Preferably, at least one beta blocker of above is used in combination with sympathicomimetic agonists which may include any agonist with an agonistic effect on α-adrenergic and/or β-adrenergic receptors, including any subtypes (e.g. $\alpha_1$-, $\alpha_2$-, $\beta_1$, $\beta_2$- and $\beta_3$-subtypes), of the sympathetic nervous system, such as but not limited to adrenaline, noradrenaline, dopamine, dobutamin, dobutrex, ephedrine and other known or yet undiscovered chemical or biological substances or compounds where any of the above mentioned are included.

The beta blockers or derivatives hereof may also be in a combination of two or more, such as three or more, four or more and five or more of any of the beta blockers discussed above.

In a specific embodiment of the present invention, the sympathicomimetic agonists comprise adrenaline and/or noradrenaline and/or dobutamine and are administered in combination with at least one beta blocker such as but not limited to a non-selective agent (i.e. may bind or block the action of more than one beta adrenergic receptor), such as, but not restricted to: Alprenolol, Carteolol, Levobunolol, Mepindolol, Metipranolol, Nadolol, Oxprenolol, Penbutolol, Pindolol, Propranolol, Sotalol, and Timolol.

In another specific embodiment of the present invention, the sympathicomimetic agonists comprise adrenaline and/or noradrenaline and/or dobutamine and are administered in combination with at least one beta blocker such as but not limited to β1-selective agents such as Acebutolol, Atenolol, Betaxolol, Bisoprolol, Esmolol, Metoprolol (Seloken), Nebivolol, Amosulalol, Landiolol, and Tilisolol; or β2-Selective agents such as Butaxamine; or beta 3 selective agents.

Most preferably, the sympathicomimetic agonists comprise adrenaline and/or noradrenaline and/or dobutamine and are administered in combination with at least one beta blocker with a high cardioselectivity (i.e. $\beta_1/\beta_2$ ratio) and low half life such as but not limited to Seloken, Esmolol and Landiolol.

In a specific embodiment of the present invention, the sympathicomimetic agonists comprise adrenaline and/or noradrenaline and/or dobutamine and the beta blocker is Seloken and/or Esmolol and/or Landiolol. The adrenaline and/or noradrenaline and/or dobutamine and Seloken and/or Esmolol and/or Landiolol are administered to prevent or treat bleeding in a subject.

In a still further embodiment of the present invention, the sympathicomimetic agonist comprises or is adrenaline and is administered in combination with Seloken.

In a still further embodiment of the present invention, the sympathicomimetic agonist comprises or is adrenaline and is administered in combination with Landiolol.

In a still further embodiment of the present invention, the sympathicomimetic agonist comprises or is adrenaline and is administered in combination with Esmolol.

In a still further embodiment of the present invention, the sympathicomimetic agonist comprises or is noradrenaline and is administered in combination with Seloken.

In a still further embodiment of the present invention, the sympathicomimetic agonist comprises or is noradrenaline and is administered in combination with Landiolol.

In a still further embodiment of the present invention, the sympathicomimetic agonist comprises or is noradrenaline and is administered in combination with Esmolol.

The terms "used in combination", "administered in combination with" or "co-administered" or "composition" indicate that the drugs may be are formulated together, or are kept as separate entities and may be administered simultaneously or within a predetermined interval of each other. Examples of how the sympathicomimetic agonists and beta blockers of the present invention may be administered in combination with each other are given in the below.

The beta blocker of the present invention that is used in combination with a sympathicomimetic for the treatment of bleeding in a subject is administered in the pharmaceutically efficient dose of the particular compound. For example, Seloken may be administered in a tablet comprising 50 mg to 200 mg of Seloken and an appropriate dosage of a sympathicomimetic agonist as disclosed above. Alternatively; Seloken may be administered parenterally at doses between 1 mg and 40 mg administered in one or several dosages or intravenously at a rate of 10 to 150 ml/hour (1 mg/ml). Likewise Esmolol (tradename Brevibloc) may be administered at 0.1 to 5.0 mg/kg as an i.v. bolus injection, such as 0.5 mg/kg and/or as between 0.01 to 1 mg/kg/min i.v., such as 0.05 to 0.3 mg/kg/min as first administration or continued administration. Similarly, Landiolol may be administered intravenously at dosages between 0.01 to 5 mg/kg/min, such as 0.1 to 0.5 mg/kg/min or as bolus injections of between 1 mg to 20 mg. As is known to a person skilled in the art, the dosage of beta blocker may be increased according the necessity thereof.

Potassium (K)

Adrenaline is known to have a lowering effect on serum potassium concentrations. Normal reference values for potassium in plasma is: 3.2-4.7 mmol/l and in serum: 3.5-5.0 mmol/l. Mild hypokalaemia (low concentration of potassium in the blood) is defined as a plasma potassium concentration>3.0 mmol/L and severe hypokalaemia is when the potassium concentration is <3.0 mmol/L. Epinephrine in the doses to be administered for the prevention and/or treatment of bleeding in a subject lowers the potassium concentration to approximately 3.3 mmol/l. and is thus not expected to cause hypokalaemia. Nevertheless, an embodiment of present invention comprises potassium at a concentration of or in an amount corresponding to between 1 mmol/L to 30 mmol/L, or 1.5 mmol/L to 25 mmol/L, or 2 mmol/L to 20 mmol/L, or 2.5 mmol/L to 15 mmol/L, or 3 mmol/L to 10 mmol/L, or 4 mmol/L to 5 mmol/L. Preferably, potassium is comprised in an amount that counter the effect of the sympathicomimetic compound and thus retains the plasma potassium concentration within the normal range. The "normal range" may be the pharmaceutically/medically accepted range of potassium concentrations found in human beings or may be individualized so the plasma concentration of potassium measured in the individual prior to commencement of treatment may be kept at the measured level.

An embodiment of the present invention relates to the administration of a sympathicomimetic agonist in a formulation comprising potassium at a concentration between 1 mmol/L and 30 mmol/L for the prevention and/or treatment of bleeding in a subject.

Thus in one aspect, the treatment of bleeding in a subject comprises the administration of at least one of the following sympathicomimetic agonists: adrenaline, noradrenaline, dopamine, dobutamin, dobutrex, and ephedrine in combination with potassium at a concentration between 1 mmol/L and 30 mmol/L. Most preferably, adrenaline and/or noradrenaline is administered in combination with potassium at a concentration of between 1 mmol/L and 30 mmol/L.

Likewise, another embodiment of the present invention relates to the administration of a sympathicomimetic agonist in combination with a beta blocker in a formulation further comprising potassium at a concentration between 1 mmol/L and 30 mmol/L for the prevention and/or treatment of bleeding in a subject.

Thus in one aspect, the treatment of bleeding in a subject comprises the administration of at least one of the following sympathicomimetic agonists: adrenaline, noradrenaline, dopamine, dobutamin, dobutrex, and ephedrine in combination a beta blocker, the blocker preferably being a beta 1 receptor specific blocker and further being administered in combination with potassium at a concentration between 1 mmol/L and 30 mmol/L. Most preferably, adrenaline and/or noradreline are administered in combination with any one of the beta blockers seloken, esmolol, landiolol and/or propanolol and further in combination with potassium at a concentration of between 1 mmol/L and 30 mmol/L.

The administration of potassium may follow that of the administration of the sympathicomimetic agonist or be independent hereof. For instance, the administration of potassium may precisely follow the administration of e.g. adrenaline such that the administration of potassium starts and/or stops with the administration of adrenaline.

For example: if the administration of adrenaline lowers the plasma potassium concentration of the individual compared to normal levels or compared to the level measured in the individual prior to adrenaline administration, potassium may be administered to counter this lowering bringing the concentration of plasma potassium back to normal. Preferably, the administration of potassium stops at the same time as the administration of the sympathicomimetic agonist and/or beta blocker.

Administration

Administration of the agonists is to be given to a subject resulting in a systemic concentration of the agonists. Methods of administration include enteral, such as oral, sublingual, gastric or rectal and/or parenterally, that is by intravenous, intramuscular, subcutaneous, intranasal, intrapulmonary, intrarectal, intravaginal or intraperitoneal administration. The subcutaneous and intravenous forms of parenteral administration are generally preferred. Appropriate dosage forms for such administration may be prepared by conventional techniques. The compounds may also be administered by inhalation that is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

As used herein, "dose" shall mean any concentration of the agonists administered producing a pro-hemostatic effect on the hemostatic system. A dose sufficient to produce the desired effect in relation to the conditions for which it is administered, in particular an amount of a sympathicomimetic agonists that is effective to stop, reduce or prevent the unwanted bleeding shall be described as the "effective dose", "therapeutically effective dose" or "effective amount". Normally the dose should be capable of preventing or lessening the severity or spread of the condition or indication being treated. The exact dose will depend on the circumstances, such as the condition being treated, the administration schedule, whether the sympathicomimetic agonists is administered alone or in conjunction with another therapeutic agent or another sympathicomimetic agonists, the plasma half-life of the sympathicomimetic agonists and the general health of the subject.

As will be understood by the person skilled in the art, amounts effective for this purpose will depend on the severity of the disease or injury as well as the weight and general state of the subject. The dose is preferably given by the parenteral administration route, notably the intravenous, intramuscular and/or the subcutaneous, sublingual, trans-mucosal, intrapulmonal and intra-alveolar route. The dosages given in the following is contemplated to be in the same order of magnitude irrespective of the parenteral administration route.

For the sympathicomimetic agonists adrenaline and noradrenaline the dose administered will for enteral and/or parenteral, notably oral, intravenous, intramuscular and/or subcutaneous routes, single or repeated bolus dose(s) be in the range of from 0.1 µg/kg to about 50 µg/kg, such as, e.g., from about 0.5 µg/kg to about 50 µg/kg, from about 1 microgram/kg to 50 microgram/kg, such as e.g. 2 microgram/kg to 20 microgram/kg, 2.5 microgram/kg to 15 microgram/kg, 3 microgram/kg to 14 microgram/kg or 3.5 microgram/kg to 13 microgram/kg, or 4 microgram/kg to 12 microgram/kg, or 4.5 microgram/kg to 11 microgram/kg, or 5 microgram/kg to 10 microgram/kg, or 5.5 microgram/kg to 9 microgram/kg, or 6 microgram/kg to 8 microgram/kg. Alternatively the parenteral, notably intravenous, intramuscular and/or subcutaneous routes, single or repeated bolus dose(s) are in the range of from 0.01 microgram/kg to 100 microgram/kg, such as 0.02 microgram/kg to 90 microgram/kg, such as 0.03 microgram/kg to 80 microgram/kg, such as 0.04 microgram/kg to 70 microgram/kg, such as 0.05 microgram/kg to 60 microgram/kg, such as 0.06 microgram/kg to 50 microgram/kg, such as 0.07 microgram/kg to 40 microgram/kg, such as 0.08 microgram/kg to 30 microgram/kg, such as 0.09 microgram/kg to 27.5 microgram/kg, such as 0.1 microgram/kg to 25 microgram/kg, such as 0.2 microgram/kg to 24 microgram/kg, such as 0.2 microgram/kg to 23 microgram/kg such as 0.3 microgram/kg to 22 microgram/kg, such as 0.4 microgram/kg to 21 microgram/kg, such as 0.5 microgram/kg to 20 microgram/kg, such as 0.6 microgram/kg to 19 microgram/kg, such as 0.7 microgram/kg to 18 microgram/kg, such as 0.8 microgram/kg to 17 microgram/kg, such as 0.9 microgram/kg to 16 microgram/kg, such as 1 microgram/kg to 15 microgram/kg. Alternatively, the interval may be between 1 microgram/kg to 20 microgram/kg, 1.5 microgram/kg to 19.5 microgram/kg, such as 2 microgram/kg to 19 microgram/kg, such as 2.5 microgram/kg to 18.5 microgram/kg, such as 3 microgram/kg to 18 microgram/kg, such as 3.5 microgram/kg to 17.5 microgram/kg, such as 4 microgram/kg to 17 microgram/kg, such as 4.5 microgram/kg to 16.5 microgram/kg, such as 5 microgram/kg to 16 microgram/kg, such as 5.5 microgram/kg to 15.5 microgram/kg, such as 6 microgram/kg to 15 microgram/kg, such as 6.5 microgram/kg to 14.5 microgram/kg, such as 7 microgram/kg to 14 microgram/kg, such as 7.5 microgram/kg to 13.5 microgram/kg, such as 8 microgram/kg to 13 microgram/kg, such as 8.5 microgram/kg to 12.5 microgram/kg, such as 9 microgram/kg to 12 microgram/kg or any interval therein between. Alternatively, for the sympathicomimetic agonists adrenaline and noradrenaline, the dose for parenteral administration, notably intravenous infusion, will be in the range of from 1 microgram/kg to 10 microgram/kg, or 1.5 microgram/kg to 9.5 microgram/kg, or 2 microgram/kg to 9 microgram/kg, or 2.5 to 8.5 microgram/kg, or 2.5 microgram/kg to 8.5 microgram/kg, or 3 microgram/kg to 8 microgram/kg, or 3.5 microgram/kg to 7.5 microgram/kg, or 4 microgram/kg to 7 microgram/kg or any interval therein between.

In an embodiment the sympathicomimetic agonists adrenaline and noradrenaline the dose administered will for intravenous, intramuscular and/or subcutaneous single or repeated bolus dose is about 1 microgram/kg.

In a specific embodiment the sympathicomimetic agonists adrenaline and noradrenaline the dose administered will for intravenous, intramuscular and/or subcutaneous routes in a single or repeated bolus dose of about 2 microgram/kg.

In a further embodiment the sympathicomimetic agonists adrenaline and noradrenaline the dose administered will for intravenous, intramuscular and/or subcutaneous single or repeated bolus dose is about 3 microgram/kg.

In a still further embodiment the sympathicomimetic agonists adrenaline and noradrenaline the dose administered will for intravenous, intramuscular and/or subcutaneous single or repeated bolus dose is about 4 microgram/kg.

In a still further embodiment the sympathicomimetic agonists adrenaline and noradrenaline the dose administered will for intravenous, intramuscular and/or subcutaneous single or repeated bolus dose is about 5 microgram/kg.

In a still further embodiment the sympathicomimetic agonists adrenaline and noradrenaline the dose administered will for intravenous, intramuscular and/or subcutaneous single or repeated bolus dose is about 6 microgram/kg.

In a still further embodiment the sympathicomimetic agonists adrenaline and noradrenaline the dose administered will for intravenous, intramuscular and/or subcutaneous single or repeated bolus dose is about 7 microgram/kg.

In a still further embodiment the sympathicomimetic agonists adrenaline and noradrenaline the dose administered will for intravenous, intramuscular and/or subcutaneous single or repeated bolus dose is about 8 microgram/kg.

In a still further embodiment the sympathicomimetic agonists adrenaline and noradrenaline the dose administered will for intravenous, intramuscular and/or subcutaneous single or repeated bolus dose is about 9 microgram/kg.

The bolus injection may be given once, twice or several times, for instance, in keeping with the dosage administered the bolus injection may be given every 5 min (minutes), such as every 10 min, such as every 15 min, such as every 20 min, such as every 25 min, such as every 30 min, such as every 35 min, such as every 40 min, such as every 45 min, such as every 50 min, such as every 55 min, such as every 60 min such as every 70 min, such as every 80 min, such as every 90 min, such as every 100 min, such as every 110 min such as every 120 min or more. For example, the bolus dosage may be administered in the appropriate intervals from the time of trauma to the subject and until a treatment facility such as a hospital or other is reached.

The bolus injection may be followed by a maintenance dose. Such dosages are described in the following; however, in specific embodiments, the following dosages may also be used without any bolus injection. For the sympathicomimetic agonists adrenaline and noradrenaline, the dose for parenteral administration, notably intravenous infusion, will be in the range of from 0.01 microgram/kg/hour to 100 microgram/kg/hour, such as 0.02 microgram/kg/hour to 90 microgram/kg/hour, such as 0.03 microgram/kg/hour to 80 microgram/kg/hour, such as 0.04 microgram/kg/hour to 70 microgram/kg/hour, such as 0.05 microgram/kg/hour to 60 microgram/kg/hour, such as 0.06 microgram/kg/hour to 50 microgram/kg/hour, such as 0.07 microgram/kg/hour to 40 microgram/kg/hour, such as 0.08 microgram/kg/hour to 30 microgram/kg/hour, such as 0.09 microgram/kg/hour to 27.5 microgram/kg/hour, such as 0.1 microgram/kg/hour to 25 microgram/kg/hour, such as 0.2 microgram/kg/hour to 24 microgram/kg/hour, such as 0.2 microgram/kg/hour to 23 microgram/kg/hour such as 0.3 microgram/kg/hour to 22 microgram/kg/hour, such as 0.4 microgram/kg/hour to 21 microgram/kg/hour, such as 0.5 microgram/kg/hour to 20 microgram/kg/hour, such as 0.6 microgram/kg/hour to 19 microgram/kg/hour, such as 0.7 microgram/kg/hour to 18 microgram/kg/hour, such as 0.8 microgram/kg/hour to 17 microgram/kg/hour, such as 0.9 microgram/kg/hour to 16 microgram/kg/hour, such as 1 microgram/kg/hour to 15 microgram/kg/hour. Alternatively, the interval may be between 1 microgram/kg/hour to 20 microgram/kg/hour, 1.5 microgram/kg/hour to 19.5 microgram/kg/hour, such as 2 microgram/kg/hour to 19 microgram/kg/hour, such as 2.5 microgram/kg/hour to 18.5 microgram/kg/hour, such as 3 microgram/kg/hour to 18 microgram/kg/hour, such as 3.5 microgram/kg/hour to 17.5 microgram/kg/hour, such as 4 microgram/kg/hour to 17 microgram/kg/hour, such as 4.5 microgram/kg/hour to 16.5 microgram/kg/hour, such as 5 microgram/kg/hour to 16 microgram/kg/hour, such as 5.5 microgram/kg/hour to 15.5 microgram/kg/hour, such as 6 microgram/kg/hour to 15 microgram/kg/hour, such as 6.5 microgram/kg/hour to 14.5 microgram/kg/hour, such as 7 microgram/kg/hour to 14 microgram/kg/hour, such as 7.5 microgram/kg/hour to 13.5 microgram/kg/hour, such as 8 microgram/kg/hour to 13 microgram/kg/hour, such as 8.5 microgram/kg/hour to 12.5 microgram/kg/hour, such as 9 microgram/kg/hour to 12 microgram/kg/hour or any interval therein between. Alternatively, for the sympathicomimetic agonists adrenaline and noradrenaline, the dose for parenteral administration, notably intravenous infusion, will be in the range of from 1 microgram/kg/hour to 10 microgram/kg/hour, or 1.5 microgram/kg/hour to 9.5 microgram/kg/hour, or 2 microgram/kg/hour to 9 microgram/kg/hour, or 2.5 to 8.5 microgram/kg/hour, or 2.5 microgram/kg/hour to 8.5 microgram/kg/hour, or 3 microgram/kg/hour to 8 microgram/kg/hour, or 3.5 microgram/kg/hour to 7.5 microgram/kg/hour, or 4 microgram/kg/hour to 7 microgram/kg/hour or any interval therein between.

In an embodiment the intravenous infusion of the sympathicomimetic agonists adrenaline and noradrenaline will be about 1 microgram/kg/hour.

In a specific embodiment the intravenous infusion of the sympathicomimetic agonists adrenaline and noradrenaline will be about 2 microgram/kg/hour.

In a further embodiment the intravenous infusion of the sympathicomimetic agonists adrenaline and noradrenaline will be about 3 microgram/kg/hour.

In a still further embodiment the intravenous infusion of the sympathicomimetic agonists adrenaline and noradrenaline will be about 4 microgram/kg/hour.

In a still further embodiment the intravenous infusion of the sympathicomimetic agonists adrenaline and noradrenaline will be about 5 microgram/kg/hour.

In a still further embodiment the intravenous infusion of the sympathicomimetic agonists adrenaline and noradrenaline will be about 6 microgram/kg/hour.

In a still further embodiment the intravenous infusion of the sympathicomimetic agonists adrenaline and noradrenaline will be about 7 microgram/kg/hour.

In a still further embodiment the intravenous infusion of the sympathicomimetic agonists adrenaline and noradrenaline will be about 8 microgram/kg/hour.

In a still further embodiment the intravenous infusion of the sympathicomimetic agonists adrenaline and noradrenaline will be about 9 microgram/kg/hour.

The infusion may be of any duration necessary such as from 1 minute (min) to several hours if required. The dosage can, due to the rapid turnover of adrenaline and similar compounds be administered continuously without risk of accumulation. Thus it is an object of the invention to infuse a subject for the prophylaxis or treatment of bleeding for more than 1 min such as 5 min, such as 10 min, such as 15 min, such as 20 min, such as 25 min, such as 30 min, such as 35 min, such as 40 min, such as 45 min, such as 50 min, such as 55 min, such as 60 min, such as 65 min, such as 70 min, such as 75 min, such as 80 min, such as 85 min, such as 90 min, such as 95 min, such as 100 min, such as 105 min, such as 110 min, such as 120 min, such as 130 min, such as 140 min, such as 150 min, such as 160 min, such as 170 min, such as 180 min, such as 190 min, such as 200 min, such as 210 min, such as 220 min, such as 230 min, such as 240 min or more.

Any sympathicomimetic able of inducing an activation of the hemostatic system equal to the above mentioned dose of adrenaline and noradrenaline i.e. dopamine at a dose of 10-100× higher (30-300 microgram/kg/hour) than adrenaline and noradrenaline and dobutamin at a dose of 10-100× higher in (30-300 microgram/kg/hour) adrenaline and noradrenaline. Based on this information it is contemplated that a person skilled in the art can choose a proper dosage.

Single or multiple administrations of the compositions and combination of sympathicomimetic agonists, beta blockers and/or potassium can be carried out with dose levels and patterns being selected by the treating physician.

The sympathicomimetic agonist and the beta blocker may be co-administered optionally in combination with potassium as soon as the subject is asleep and the administration may be stopped after last suture.

The combination of sympathicomimetic agonist and beta blocker acts instantaneously with regard to development of the pro-hemostatic response, and development of tachycardia/tachyarrythmia is prevented by an initial loading dose of the beta blocker starting prior to the administration of the sympathicomimetic agonist followed by a continuous infusion. Thus, due to i.e. differences in turn over rate of the sympathicomimetic agonist and the beta blocker (the beta blocker in the following example having the longer turn over rate) and optionally the potassium may be administered such that the blocker is administered for a number of minutes (between 1 and 5 minutes) prior to administration of the sympathicomimetic agonist and likewise towards the end of the treatment, the administration of the blocker is discontinued first, for example 5 to 20 minutes before stopping the administration of the sympathicomimetic agonist. The potassium may be co-administered with the sympathicomimetic agonist.

Likewise, the pro-hemostatic effect of the sympathicomimetic agonist/beta blocker is abated within a well defined time after discontinuation of the infusion and the administration of the blocker will therefore be adjusted so the blockage of the cardiac beta receptors is reversed when the haemodynamic effect of the sympathicomimetic agonist is abated. It will therefore be possible to discontinue the infusion of the sympathicomimetic agonist/beta blocker, well before the surgical procedure is finalized and bleeding has been controlled and the pro-hemostatic effect of the product will not be measurable by TEG MA 30-60 min postoperatively.

In prophylactic applications, compositions containing the sympathicomimetic agonist of the invention are administered to a subject susceptible to or otherwise at risk of a disease state or injury to enhance the subject's own hemostatic capability. Such an amount is defined to be a "prophylactically effective dose." In prophylactic applications, the precise amounts once again depend on the subject's state of health and weight, and it is anticipated that the dose generally will be as specified above.

The beta blockers of the present invention may be administered in the dosages recommended by the manufacturers or as are known to be efficient to those skilled in the art, i.e. medical practitioners.

Pharmaceutical Compositions of the Invention and its Use

The present invention also relates to a pharmaceutical composition comprising one or more sympathicomimetic agonists and one or more pharmaceutically acceptable carriers or exipients. Such pharmaceutically acceptable carrier or excipient as well as suitable pharmaceutical formulation methods are well known in the art (see for example Remington: The Science and Practice of Pharmacy 1995, edited by E. W. Martin, Mack Publishing Company, 19th edition, Easton, Pa. In a preferred embodiments the sympathicomimetic variant are prepared in a parenteral composition. Such methods for preparing parenterally administrable compositions will also be known or apparent to those skilled in the art and are described in more detail in, for example, Remington's Pharmaceutical Sciences, 18th ed., Mack Publishing Company, Easton, Pa. (1990). As used herein, the term "pharmaceutical acceptable" means a carriers or excipients that does not cause any untoward effects in subjects to whom it is administered.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The compositions for parenteral administration comprise the agonist of the invention in combination with, preferably dissolved in, a pharmaceutically acceptable carrier, preferably an aqueous carrier. A variety of aqueous carriers may be used, such as water, buffered water, lactated Ringer's solution, saline, e.g. such as 0.7%, 0.8%, 0.9% or 1%, glycine such as 0.2%, 0.3%, 0.4% or 0.5% and the like. Normally, it is aimed that the composition has an osmotic pressure corresponding to a 0.9% w/w sodium chloride solution in water. Moreover, as known by a person skilled in the art, dependent on the specific administration route, pH may be adjusted within suitable ranges centered around pH 7.4. The compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The sympathicomimetic agonist and/or beta blocker and/or potassium may be formulated so it can be stored at room temperature in preformed bags or syringes containing the solution with the sympathicomimetic agonist and/or beta blocker and/or potassium. The bag may be compartmentalized enabling an initial loading dose of the beta blocker before infusion of the sympathicomimetic agonist and/or potassium commence. Likewise, the syringe may be for single or dual injections and optionally allowing premixing of sympathicomimetic agonist and beta blocker. The concentration of the sympathicomimetic agonist and beta blocker is predefined enabling immediate dosing based on the patients weight regardless of age and gender. The preformed bag may be a 1 liter or a 500 ml or any other conventionally sized bag formulated to tolerate light and be stable at room temperature. The syringe may be a 50 ml syringe, or a syringe of any conventional size such as between 10 ml and 100 ml.

The pharmaceutical composition may also be formulated in other forms e.g. as a gel, liquid, or as compressed solid. The preferred form will depend upon the particular indication being treated and will be apparent to one skilled in the art.

The compositions may contain pharmaceutically acceptable auxiliary substances as required to approximate physiological conditions, such as pH adjusting and buffering agents, stabilizing agents, preservatives, non-ionic surfactants or detergents, antioxidants, tonicity adjusting agents and the like, for example, sodium acetate, sodium lactate, sodium chloride, potassium chloride, calcium chloride, etc.

The sympathicomimetic agonists may also be in a salt form thereof. Suitable salts include, but are not limited to, salts with alkali metals or earth metals, such as sodium, potassium, calcium and magnesium as well as e.g. zinc salts. These salts or complexes may be present as a crystalline and/or amorphous structure.

Administration of the sympathicomimetic agonists for the treatment of bleeding episodes may either be the sole treatment or in any combination with other therapeutic agents such as red blood cells, and/or plasma and/or platelets and/or other procoagulants such as any of the coagulation factors alone or in combination and/or antifibrinolytics such as aprotinin, tranexamic acid amino caproic acid, and or vasoconstrictors.

These agents may be incorporated as part of the same pharmaceutical composition or may be administered separately from the sympathicomimetic agonists, either concurrently or in accordance with another treatment schedule.

The sympathicomimetic agonists are primarily intended for parenteral administration for prophylactic and/or therapeutic treatment. Preferably, the sympathicomimetic agonists are administered parenterally, i.e., intravenously, subcutaneously, or intramuscularly, sublingual, mucosaaplication, intrapulmonary and it may be administered by continuous or pulsatile infusion. The sympathomimetic agonists can be administered separately or in any combination both for therapeutic or prophylactic use.

In another aspect of the present invention, it has been found that clot strength is better correlated with postoperative coagulopathic bleeding in subjects than conventional coagulation analysis including prothrombin time (PT), activated partial thromboplastin time (APTT), platelet count and fibrinogen levels undergoing cardiac surgery (Welsby et al. 2006). The clot strength can be approached by use of e.g. thrombelastography (TEG), as will be explained in details in the examples herein. Adhering to a transfusion algorithm aiming at a normal TEG clot strength reduces bleeding and postoperative transfusion requirements in cardiac surgery, liver transplantation and in critically ill patients as shown by Shore-Lesserson et al. (1999), Kang (1995) and Johansson et al. (2007).

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound(s). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound(s) with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Examples of a Typical Tablet

A typical tablet which may be prepared by conventional tabletting techniques may contain:

Core:

| | |
|---|---|
| Sympathicomimetic agonist (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |

Coating:

| | |
|---|---|
| HPMC approx. | 9 mg |
| *Mywacett 9-40 T approx. | 0.9 mg |

*Acylated monoglyceride used as plasticizer for film coating.

Optionally a beta blocker and/or potassium may also be included in the formulation.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100. degree C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The Pharmaceutical Carrier

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form. Several scenarios can be envisaged where administration of a sympathicomimetic agonist and/or a beta blocker and/or potassium would be of benefit to a bleeding subject. One is in the hospital/clinic or other similarly well supervised conditions where the subject either will be undergoing planned surgery or is admitted in a state that requires surgery. In such instances an embodiment of the present invention comprising a sympathicomimetic agonist and/or a beta blocker and/or potassium in a pre-prepared and ready to use solution such as in an infusion bag or pre-prepared syringe will be preferable. The pre-prepared solution may then be administered prior to, during or after surgery.

A specially preferred embodiment of this aspect of the present invention comprises a pre-prepared formulation of a sympathicomimetic agonist and a beta blocker and/or potassium that may be stored at ambient temperature, i.e. room temperature, and which also is unaltered (i.e. the compounds do not degrade/breakdown become metabolized or otherwise loose their activity) if exposed to light. Furthermore it is preferred if the formulation is such that it may be administered in the correct dosage immediately, for example at a dosage of 3 microgram/kg/hour.

Another scenario is following a situation of emergency such as a traffic accident, military exercise or warfare where the bleeding subject will benefit from immediate staunching of the bleeding. In this scenario, a pre-prepared formulation may be of a sympathicomimetic agonist and/or a beta blocker and/or potassium, preferably just a sympathicomimetic agonist in a form that allows immediate administration i.e. in a pre-prepared syringe (for i.e. intra muscular, intravenous or subcutaneous administration) or tablet or other mucosal application form. This formulation may be administered to the subject at the scene, in an ambulance or helicopter.

An embodiment of the invention thus relates to a pre-prepared syringe with a content befitting the average adult or child human being. The average adult human being may thus way 70 kg and therefore the pre-prepared syringe may have a content of between 210 and 3150 microgram adrenaline is a suitable volume. The average adult or child human weight after which the amount of sympathicomimetic agonist is calculated may be adapted to suit specific circumstances such as children of different age groups (they are expected to increase in weight with age) or different nationalities, as different nations have different mean weights of their inhabitants. The same amount of adrenaline or noradrenaline or any sympathicomimetic may correspondingly be pressed into a tablet. Likewise, a pre-prepared syringe may be made for the specific purpose of having a duration of 5 min, 10 min, 15 min, 30 min, or 60 min or anything therein between.

Embodiments of Use

The sympathicomimetic agonists and/or beta blockers and/or potassium combinations are particular suitable for the treatment and/or prophylaxis of bleeding, including uncontrolled and excessive bleeding episodes in connection with surgery and other forms of tissue damage. In the following is provided a non-exhaustive description of various conditions were sympathicomimetic agonists and/or beta blockers and/or potassium combinations, either administered alone or in combination with any of the above mentioned treatments, are envisaged to be beneficial in controlling or preventing bleedings, due to their above-described systemic hemostatic properties.

Treatment of Bleeding Caused by Trauma

In subjects who experience extensive tissue damage in association with surgery or vast trauma, the normal hemostatic mechanism may be overwhelmed by the demand of immediate hemostasis and they may develop bleeding in spite of a normal hemostatic mechanism. It is envisaged that in any form of trauma, systemic administration of sympathicomimetic agonists may be beneficial to the subject. As used herein, the term "trauma" is intended to mean injury to living tissue caused by an extrinsic agent.

Hemorrhage as a result of trauma can start a cascade of problems. For example physiological compensation mechanisms are initiated with the initial peripheral mesenteric vasoconstriction to shunt blood to the central circulation. If circulation is not restored, hypovolaemic shock ensures (multiple organ failure due to inadequate perfusion.) Trauma patients may develop hypothermia due to environmental conditions at the scene, inadequate protection, intravenous fluid and blood product administration and ongoing blood loss. Deficiencies in coagulation factors and platelets can result from blood loss, dilution, consumption or transfusions. Meanwhile acidosis and hypothermia interfere with normal blood clotting mechanisms. Thus coagulophathy develops which may mask surgical bleeding sites and hamper control of mechanical bleeding. Hypothermia, coagulophathy and acidosis are often characterized as the "lethal triad" as these conditions often lead to uncontrollable blood loss, multiple organ failure and death typically in an intensive care unit.

In addition to hypovolaemic shock as a result of blood loss, shock may also develop as a result of activation of the inflammatory pathways, resulting in a hypocoagulant state. This subset of trauma patients has particularly high mortality.

One general aspect of the invention therefore relates to methods of treatment of bleeding in patients suffering from various forms of trauma.

In one embodiment, the invention thus relates to a method for the treatment of bleeding caused by trauma in a subject, comprising administering to said subject a sympathicomimetic agonist and/or a beta blocker and/or potassium.

In one embodiment, the invention thus relates to a method for the treatment of bleeding caused by trauma towards the head and/or neck including but not limited to the brain, eye(s), ear(s), nose, mouth, esophagus, trachea, soft tissues, muscles, bones and/or vessel(s) in a subject, comprising administering to said subject a sympathicomimetic agonist and/or a beta blocker and/or potassium.

In one embodiment, the invention thus relates to a method for the treatment of bleeding caused by trauma towards the thoracic region including but not limited to the heart, lungs, esophagus, soft tissues, muscles or any vessel or vessels in a subject, comprising administering to said subject a sympathicomimetic agonist and/or a beta blocker and/or potassium.

In one embodiment, the invention thus relates to a method for the treatment of bleeding caused by trauma towards the abdomen including but not limited to the liver, pancreas, spleen, ventricle, gall-bladder, intestines, or retroperitoneal tissue, soft tissues, muscles or any vessel or vessels in a subject, comprising administering to said subject a sympathicomimetic agonist and/or a beta blocker and/or potassium.

In one embodiment, the invention thus relates to a method for the treatment of bleeding caused by trauma towards the pelvis including but not limited to prostate, urinary bladder, uterus, ovarii, bones i.e. pelvic ring, hip, femur, soft tissues, muscles or any vessel or vessels in a subject, comprising administering to said subject a sympathicomimetic agonist and/or a beta blocker and/or potassium.

In one embodiment, the invention thus relates to a method for the treatment of bleeding caused by trauma towards the long bones of the extremities including but not limited to humerus, ulnae, radii and/or bones of the hand, femur, tibia, fibula and/or bones of the foot, the columnae, scapulae, costae, clavicle or in any combination hereof in a subject, comprising administering to said subject a sympathicomimetic agonist and/or a beta blocker and/or potassium.

In one embodiment, the invention thus relates to a method for the treatment of bleeding caused by trauma towards any combination of the above in a subject, comprising administering to said subject a sympathicomimetic agonist and/or a beta blocker and/or potassium.

In another embodiment, the invention relates to a method for the treatment of subjects suffering from shock as a result of blood loss after trauma comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding in connection with any of the indications discussed above.

Treatment of Bleedings in the Brain and Central Nervous System

Intracerebral hemorrhage (ICH) is the most deadly form of stroke. In addition to high short-term mortality rates, ICH also results in very high rates of severe mental and physical disability among survivors. The causes of ICH are numerous and can include head trauma, traumatic brain injury (TBI), hypertensive hemorrhage, transformation of prior ischemic infarction (ischemic stroke), metastatic brain tumor, coagulophathy, drug induced ICH, arteriovenous malformation, aneurysm, amyloid angiopathy, cavernous angioma, dural arteriosvenous fistula and capillary telaniectasias.

A further embodiment of this aspect of the invention relates to methods for the treatment of primary intracerebral bleeding (ICH) in a subject, comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding in connection with any of the ICH-related causes of a subject as discussed above.

Treatments of Surgical Bleeds

Another situation is when subjects are to undergo elective or acute surgical interventions where bleeding may occur and hence where administration of blood products may become necessary. The surgery may be either a scheduled or acute procedure, and may be any type of surgery on any part of the body.

One embodiment of this aspect of the invention thus relates to methods for the treatment of a subject in connection with surgical inventions, comprising administering to said subject a sympathicomimetic agonist and/or a beta blocker and/or potassium.

Additionally, the invention relates to use of sympathicomimetic agonists and/or beta blockers and/or potassium for the preparation of a medicament for the treatment of bleeding in connection with surgery as discussed above.

One general aspect of the invention therefore relates to methods of treatment of bleeding in patients suffering from/undergoing various forms of surgery.

In one embodiment, the invention thus relates to a method for the treatment of bleeding caused by surgery in a subject, comprising administering to said subject a sympathicomimetic agonist and/or a beta blocker and/or potassium.

In one embodiment, the invention thus relates to a method for the treatment of bleeding caused by surgery in the head and/or neck including but not limited to the brain, eye(s), ear(s), nose, mouth, esophagus, trachea, bones, soft tissue, muscles and vessel(s) in a subject, comprising administering to said subject a sympathicomimetic agonist and/or a beta blocker and/or potassium.

In one embodiment, the invention thus relates to a method for the treatment of bleeding caused by surgery in the thoracic region including but not limited to the heart, lungs, esophagus, soft tissue, muscles or any vessel or vessels in a subject, comprising administering to said subject a sympathicomimetic agonist and/or a beta blocker and/or potassium.

In one embodiment, the invention thus relates to a method for the treatment of bleeding caused by surgery in the abdomen including but not limited to the liver, pancreas, spleen, kidney, adrenal glands, ventricle, gall-bladder, intestines, retroperitoneal tissue, soft tissue, muscles or any vessel or vessels in a subject, comprising administering to said subject a sympathicomimetic agonist and/or a beta blocker and/or potassium.

In one embodiment, the invention thus relates to a method for the treatment of bleeding caused by surgery in the pelvis including but not limited to prostate, urinary bladder, uterus, ovarii, bones i.e. pelvic ring, hip, femur, soft tissue, muscles or any vessel or vessels in a subject, comprising administering to said subject a sympathicomimetic agonist and/or a beta blocker and/or potassium.

In one embodiment, the invention thus relates to a method for the treatment of bleeding caused by surgery of the long bones of the extremities including but not limited to humerus, ulnae, radii and/or bones of the hand, femur, tibia, fibula and/or bones of the foot, the columnae, scapulae, costae, clavicle, soft tissue, muscles or in any combination hereof in a subject, comprising administering to said subject a sympathicomimetic agonist and/or a beta blocker and/or potassium.

In one embodiment, the invention thus relates to a method for the treatment of bleeding caused by surgery in any combination of the above in a subject, comprising administering to said subject a sympathicomimetic agonist and/or a beta blocker and/or potassium.

Additionally, the invention relates to use of sympathicomimetic agonists and/or beta blockers and/or potassium for the preparation of a medicament for the treatment of bleeding in connection with surgery as discussed above.

Treatment of Bleedings Associated with Vascular Defects

Bleeding secondary to vascular defects may arise due to congenital or acquired defects of the vascular system resulting in aneurysms of arteries and or veins, arterioveinuous malformations or rupture of atherosclerotic plaques. These bleedings may be severe or life-threatening depending on localization i.e. intracerebral and/or the size of vessel(s) affected, exemplified by ruptured aortic lesions.

One embodiment of this aspect of the invention thus relates to methods for the treatment of a subject in connection with vascular defects, comprising administering to said subject a sympathicomimetic agonist and/or a beta blocker and/or potassium.

Additionally, the invention relates to use of sympathicomimetic agonists and/or beta blockers and/or potassium for the preparation of a medicament for the treatment of bleeding in connection with vascular defects as discussed above.

One general aspect of the invention therefore relates to methods of treatment of bleeding in patients suffering from various forms of vascular defects.

In one embodiment, the invention thus relates to a method for the treatment of bleeding caused by vascular defects in a subject, comprising administering to said subject a sympathicomimetic agonist and/or a beta blocker and/or potassium.

In one embodiment, the invention thus relates to a method for the treatment of bleeding caused by vascular defects in the head and/or neck region including, but not limited to the brain, eye(s), ear(s), nose, mouth, esophagus, trachea, soft tissue or muscles in a subject, comprising administering to said subject a sympathicomimetic agonist and/or a beta blocker and/or potassium.

In one embodiment, the invention thus relates to a method for the treatment of bleeding caused by vascular defects in the thoracic region including but not limited to the heart, lungs, esophagus, soft tissue or muscles or any other vessel or vessels in a subject, comprising administering to said subject a sympathicomimetic agonist and/or a beta blocker and/or potassium.

In one embodiment, the invention thus relates to a method for the treatment of bleeding caused by vascular defects in the abdomen including but not limited to the liver, pancreas, spleen, kidney, adrenal glands, ventricle, gall-bladder, intestines, retroperitoneal tissue, soft tissue or muscles or any other vessel or vessels in a subject, comprising administering to said subject a sympathicomimetic agonist and/or a beta blocker and/or potassium.

In one embodiment, the invention thus relates to a method for the treatment of bleeding caused by vascular defects in the pelvis including but not limited to prostate, urinary bladder, uterus, ovarii, bones i.e. pelvic ring, hip, femur, soft tissue or muscles or any vessel or vessels in a subject, comprising administering to said subject a sympathicomimetic agonist and/or a beta blocker and/or potassium.

In one embodiment, the invention thus relates to a method for the treatment of bleeding caused by vascular defects in the soft tissue and/or muscles surrounding of the long bones of the extremities including but not limited to humerus, ulnae, radii and/or bones of the hand, femur, tibia, fibula and/or bones of the foot, the columnae, scapulae, costae, clavicle, soft tissue or muscles or in any combination hereof in a subject, comprising administering to said subject a sympathicomimetic agonist and/or a beta blocker and/or potassium.

In one embodiment, the invention thus relates to a method for the treatment of bleeding caused by vascular defects in any combination of the above in a subject, comprising administering to said subject a sympathicomimetic agonist and/or a beta blocker and/or potassium.

Additionally, the invention relates to use of sympathicomimetic agonists and/or beta blockers and/or potassium for the preparation of a medicament for the treatment of bleeding in connection with various forms of vascular defects discussed above.

Treatment of Bleeding Associated with Biopsies and Laparoscopic Surgery

A further aspect of the invention relates to methods of treatment of bleeding in subject undergoing biopsies from various organs (brain, heart, liver, lung, pancreas, spleen, lymphoid tissue, intestines, adrenal glands, tumors, soft tissue, muscles, gastrointestinal tract) as well as in laparoscopic surgery.

In one embodiment, the invention thus relates to a method for the treatment of bleeding in subjects undergoing biopsies, comprising administering to said subject a sympathicomimetic agonist and/or a beta blocker and/or potassium.

In another embodiment, the invention relates to a method for the treatment of bleeding in subjects undergoing laparoscopic surgery, comprising administering to said subject a sympathicomimetic agonist and/or a beta blocker and/or potassium.

In an additional embodiment, the invention relates to the use of sympathicomimetic agonists and/or beta blockers and/or potassium for the preparation of a medicament for treatment of bleeding as a in a subject undergoing biopsies as discussed above or undergoing laparoscopic surgery.

Treatment of Bleeding Caused by Coagulopathy

Uncontrolled and/or excessive bleeding may occur in subjects having a normal coagulation system and subjects having coagulation or bleeding disorders. Excessive bleedings may also occur in subjects with a normally functioning blood clotting cascade (no clotting factor deficiencies or -inhibitors against any of the coagulation factors).

Bleeding secondary to coagulopathy i.e. coagulation factor dilution with crystalloids and or colloids and/or blood products and/or consumption such as but not limited to infection, sepsis, DIC (disseminated intravascular coagulation), haematological disorders and malignancies, graft vs. host disease, and/or congenital or acquired coagulation factor deficiency such as but not limited to haemophilia A or B, inhibitors against coagulation factors.

In one embodiment, the invention relates to a method for the treatment of bleeding in a coagulopathic subject, comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding in a coagulopathic subject.

Treatment of Bleeding as a Consequence of Treatment with Anticoagulants/Antithrombotics Bleeding, also acute and/or profuse may also occur in subjects on anticoagulant therapy in whom a defective hemostasis has been induced by the therapy given. Such subjects may need surgical interventions in case the anticoagulant effect has to be counteracted rapidly. Another situation that may cause problems in the case of unsatisfactory hemostasis is when subjects with a normal hemostatic mechanism are given anticoagulant therapy to prevent thromboembolic disease. Such therapy may include heparin both unfractionated and low molecular weight, other forms of proteoglycans, activated protein C, antithrombin, tissue factor pathway inhibitor, warfarin or other forms of vitamin K-antagonists as well as aspirin, dipyrimidol, NSAID, GPIIb/IIIa inhibitors, Flolan (prostacyclin) ADP receptor inhibitors, direct thrombin inhibitors, hirudin, citrate, and other platelet activation/aggregation inhibitors. A further general aspect of the invention therefore relates to methods of treatment of bleeding in connection with anticoagulant therapy.

In one embodiment, the invention thus relates to a method for treatment of bleeding in a subject receiving an anticoagulant and antithrombotic drug, comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding complication due to anticoagulant treatment in a subject.

Treatment of Thrombocytopenic Subjects

Thrombocytopenic subjects are characterized by a reduced blood platelet (thrombocyte) count resulting from a reduced platelet production and/or an increased loss of platelets. There are numerous causes of thrombocytopenia such as decreased bone marrow production of megakaryocytes (e.g. due to marrow infiltration with tumor or fibrosis, or marrow failure induced by e.g. aplasia, hypoplastic anemias, or chemotherapy or other drugs), splenic sequestration of circulating platelets (e.g. splenic enlargement due to tumor infiltration or plenic congestion due to portal hypertension), increased destruction of circulating platelets (e.g. due to vascular prosthese, cardiac valves, disseminated intravascular coagulation (DIC), sepsis, vasculitis, autoantibodies to platelets, drug-associated antibodies, or circulating immune complexes induced by systemic lupus erythematosis, viral agents, bacterial sepsis or idiopathic thrombocytopenic pupora (ITP), platelet disorders, von Willebrands disease, Bernhard-Soulier syndrome, Glanzmann's thrombasthenia, decreased cyclooxygenase activity (drug induced or congenital), granule storage pool defects (acquired or congenital), uremia, platelet coating (e.g. due to penicillin or paraproteins), defective platelet coagulant activity (Scott's syndrome, or thrombocytopenia associated with liver disease such as caused by hepatitis C or hepatitis B, or caused by IFN-alpha treatment of hepatitis C or hepatitis B as well as secondary to hypersplenism Another general aspect of the invention thus relates to treatment of bleeding in connection with thrombocytopenia caused by e.g. any of the conditions discussed above.

In one embodiment, the invention thus relates to a method for treatment of bleeding in connection with thrombocytopenia in a subject, comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding in connection with thrombocytopenia caused by e.g. any of the conditions discussed above.

Another aspect of the invention relates to the treatment of bleeding in a subject caused by a combination of coagulopathy (coagulation factor deficiency) and thrombocytopenia (low platelet count) or due to low platelet function In one embodiment, the invention thus relates to a method for treatment of bleeding in connection with a combination of coagulopathy (acquired or congenital) and thrombocytopenia (acquired or congenital) in a subject, comprising administering to said subject a sympathicomimetic agonist and/or a beta blocker and/or potassium.

In an additional embodiment, the invention relates to the use of sympathicomimetic agonists for the preparation of a medicament for treatment of bleeding in connection with coagulopathy (acquired or congenital) and thrombocytopenia (acquired or congenital) caused by e.g. any of the conditions discussed above.

Treatment of Bleedings Associated with Transplantation

Patients undergoing transplantation of solid organs, such as but not limited to liver, heart, lungs, pancreas, kidneys and/or intestines are at high risk of developing bleeding due to the surgically induced bleeding. Also patients undergoing hematopoietic stem cell or bone marrow transplantation are at risk of bleeding due to the conditioning of the patients with body irradiation and chemotherapy eradicating the patients hematopoietic system and hence severely deficient of platelets and red blood cells. In the post-transplant period these patients are at risk of developing graft vs. host disease, which may result in bleedings from the liver, gastrointestinal and urogenital system as well as from the bronchioalveolar system.

In one embodiment, the invention thus relates to a method for treatment of bleeding in connection with solid organ or hematopoietic system transplantation in a subject, comprising administering to said subject a sympathicomimetic agonist and/or a beta blocker and/or potassium.

In an additional embodiment, the invention relates to use of sympathicomimetic agonists and/or beta blockers and/or potassium for the preparation of a medicament for treatment of bleeding in connection with solid organ or hematopoietic system transplantation caused by e.g. any of the conditions discussed above.

DETAILED DESCRIPTION OF THE DRAWINGS

FIG. 1: TEG technology. See Example 1 for explanation.

Figure 2:
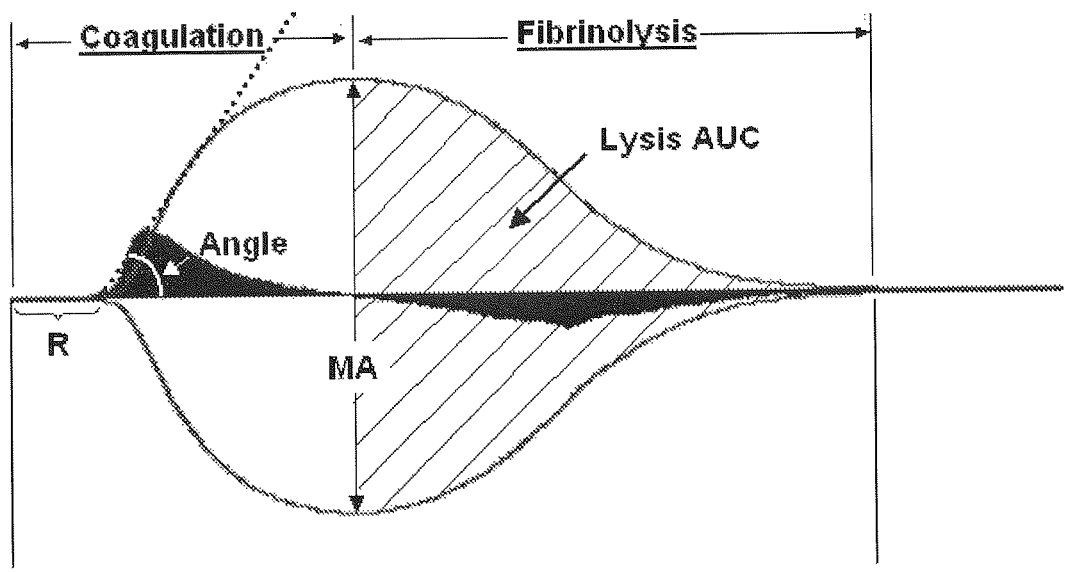
FIG. 2: TEG parameters.

FIG. 2: TEG parameters. The following parameters are derived from a TEG tracing; R, the time from start of analysis until initial clot formation (at 2 mm amplitude); Angle, representing velocity of clot formation; MA, maximal amplitude, the maximal physical clot strength; Lysis AUC, the area under the fibrinolysis curve calculated from MA (hatched area).

Figure 3:
FIG. 3: Representative TEG profile of healthy volunteers before and after administration of sympathicomimetics agonists.

FIG. 3: Representative TEG profile of healthy volunteers before and after administration of adrenaline. Whole blood was drawn in 1/10 citrate from an arterial catheter. The citrated whole blood sample rested exactly 30 minutes at room temperature before TEG analysis on the Thrombelastograph Hemostasis Analyser, series 5000 (Haemoscope Corp., Skokie, Ill.): One ml of citrated whole blood was transferred to a kaolin vial (Haemoscope Corp.) and gently mixed by inversion 5 times. From the kaolin vial 340 µl was added to a plain TEG cup preloaded with 20 µl of 0.2 M $CaCl_2$ and the analysis started immediately.

Figure 4:
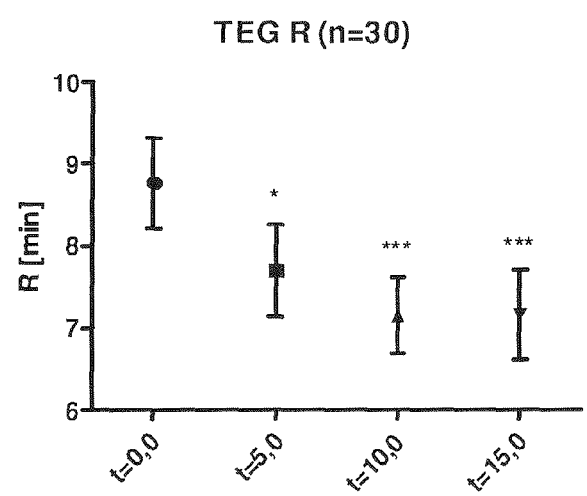
FIGS. 4a, b, and c: TEG parameters (4a) R, (4b) Angle and (4c) MA of 30 healthy volunteers after totally 15 minutes of i.v. administration of adrenaline.
Figure 4:
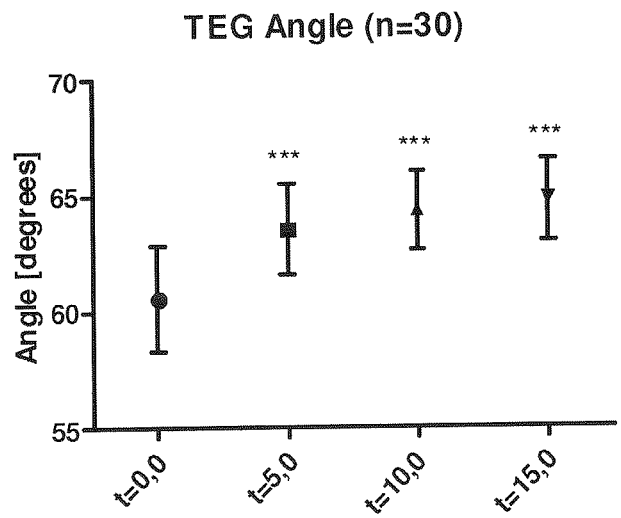
Figure 4:
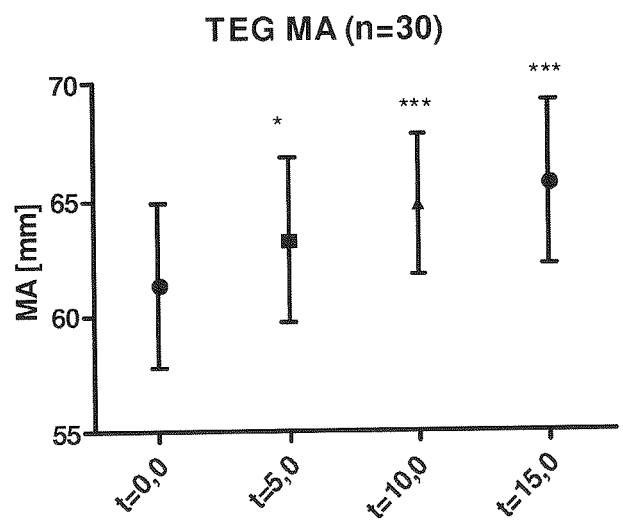

FIG. 4: TEG parameters (a) R, (b) Angle and (c) MA of 30 healthy volunteers after totally 15 minutes of i.v. administration of adrenaline. The subjects were catheterized and rested 60 minutes before administration of adrenaline was commenced. Adrenaline was step-wise infused intravenously for 5 minutes at each of the doses 3.5 µg/kg/h, 5.0 µg/kg/h and 6.0 µg/kg/h. Blood samples were collected from an arterial catheter at baseline (t=0) and immediately after each dose (t=5, t=10 and t=15). Results are presented as mean with 95% confidence interval (CI) and analyzed by 1-way ANOVA (Friedman), followed by post hoc Dunn's Multiple Comparison Test, t=0 vs t=5, t=10 and t=15 respectively, *p<0.05, ***p<0.001.

Figure 5:
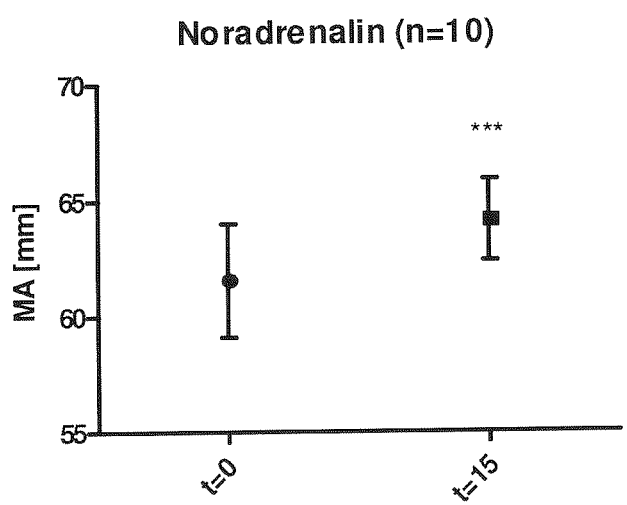
FIG. 5: TEG MA measured before and after i.v. infusion of noradrenaline at 4.8 µg/kg/h for 15 minutes in 10 healthy volunteers.

FIG. 5: TEG MA measured before and after i.v. infusion of noradrenaline at 4.8 µg/kg/h for 15 minutes in 10 healthy volunteers, mean with 95% CI. MA before and after noradrenaline was compared by a paired t-test with a p-value<0.05 considered statistically significant.

Figure 6:
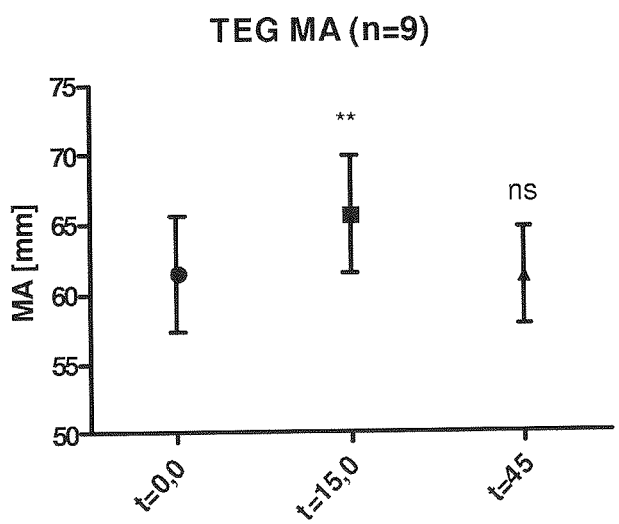
FIG. 6: TEG MA measured before (t=0) and after i.v. infusion of adrenaline at 4.8 µg/kg/h for 15 minutes (t=15) and 30 minutes after discontinuation of adrenaline administration (t=45).

FIG. 6: TEG MA measured before (t=0) and after i.v. infusion of adrenaline at 4.8 µg/kg/h for 15 minutes (t=15) and 30 minutes after discontinuation of adrenaline administration (t=45). Data presented as mean with 95% CI. Friedman 1-way ANOVA and Bonferroni post hoc test was used for comparing t=0 to t=15 and to t=45, respectively, **p<0.01, ns; non significant.

FIG. 7: TEG parameters (a) R, (b) Angle and (c) MA measured as described in FIG. 3 and example 1 on blood samples collected from patients infused with adrenaline prior to prostatectomy. Ten patients were anesthetized by propofol and haldid and infused with adrenaline i.v. in the doses 1, 2 and 3 µg/kg/h each for 5 minutes prior to skin incision. Hereafter the patients were prostatectomised according to local protocol. Blood samples were collected from an arterial catheter before adrenaline administration and immediately after each infusion dose (1, 2 and 3 µg/kg/h) and again 1 hour after discontinuation of adrenaline infusion. Statistics used: One-way ANOVA, Friedman Test, and Dunn's Multiple Comparison post hoc test of "before" compared to each of the following points 1, 2, 3 µg/kg/h and 1 hour after termination of adrenaline infusion, *p<0.05, p<0.01, *p<0.001, ns: non significant.

Figure 7A:
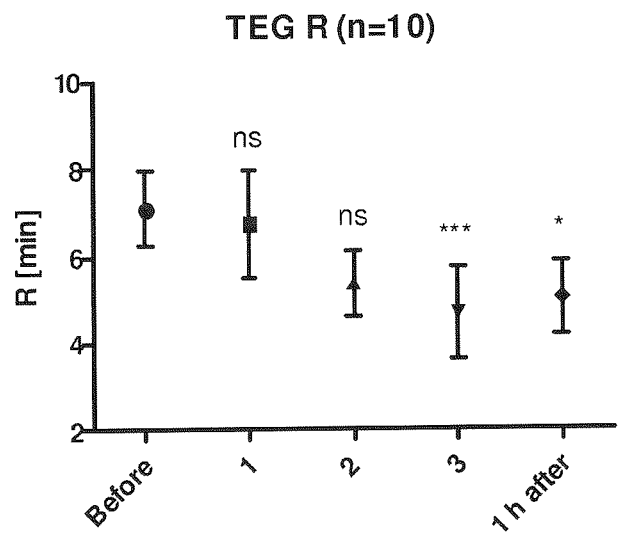
FIGS. 7 a, b and c: TEG parameters (7a) R, (7b) Angle and (7c) MA from blood samples collected from patients infused with adrenaline prior to prostatectomy.
Figure 7B:
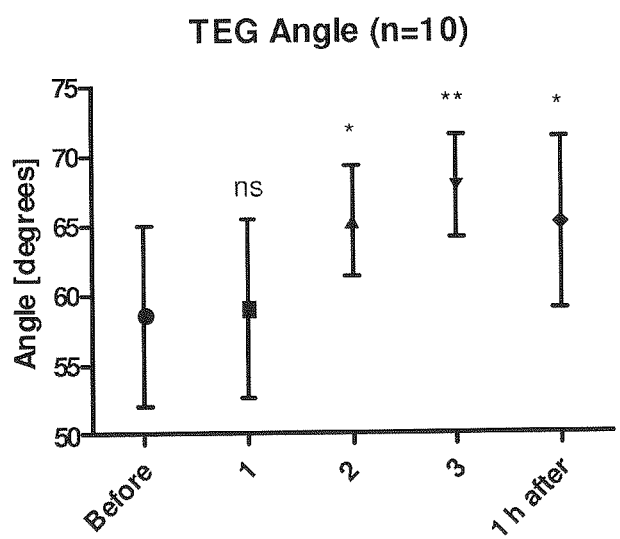
Figure 7C:
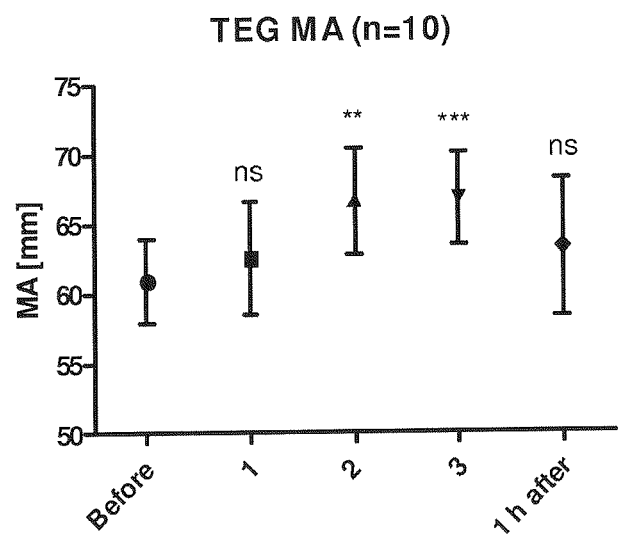
Figure 8:
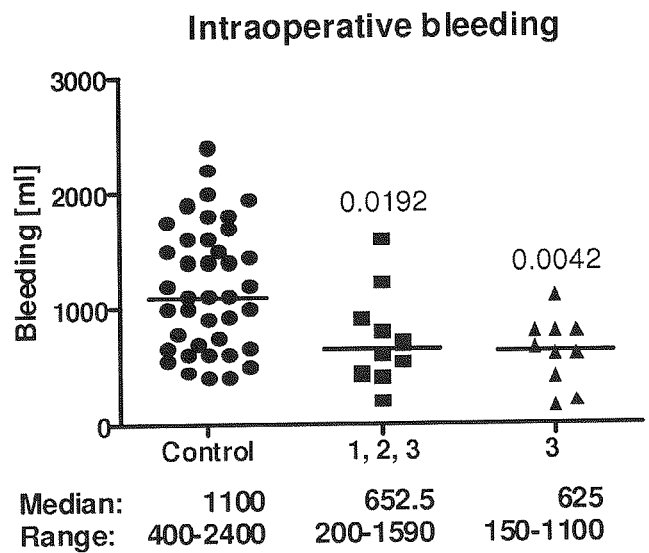
FIG. 8: Intra-operative bleeding (in ml) of the patients of FIG. 7 (receiving adrenaline in the step-wise doses 1, 2 and 3 µg/kg/h) and 10 other prostatectomy patients receiving a 15 minutes continuous adrenaline infusion of 3 µg/kg/h.

FIG. 8: Perioperative bleeding (in ml) of the 10 patients described in FIG. 7 (receiving adrenaline in the step-wise doses 1, 2 and 3 µg/kg/h) and 10 other prostatectomy patients receiving a 15 minutes continuous adrenaline infusion of 3 µg/kg/h. The 2 intervention groups were compared to 40 controls also undergoing prostatectomy, whereof 20 underwent surgery prior to the interventions and the last 20 after the intervention. All values including median for each group is depicted. Comparisons between control group and each of the intervention groups was done separately by Mann Whitney test.

Figure 9A:
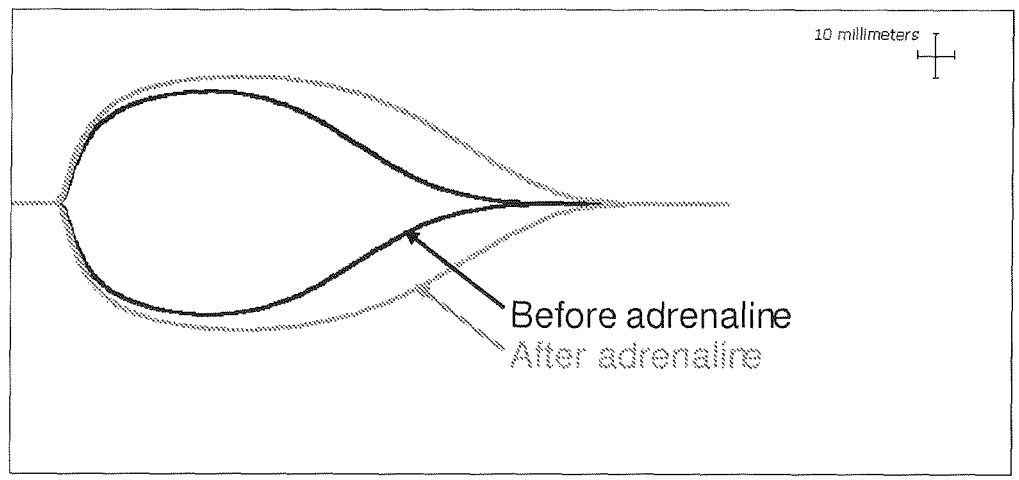
FIGS. 9 a and b: (9a) A representative example of TEG tracings with tPA induced fibrinolysis before and immediately after infusions of adrenaline. (9b) Statistic comparisons of the lysis AUC (area under the curve).
Figure 9B:
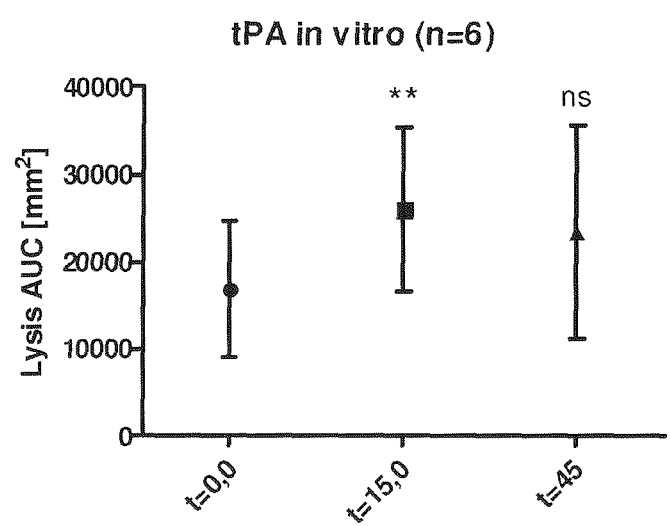

FIG. 9: Healthy volunteers received adrenaline as described in FIG. 4. Arterial blood was collected in citrate before and after the last adrenaline dose (t=15) and again 30 minutes after end of infusion (t=45). The blood was analyzed with TEG (described in FIG. 3) after addition of tissue plasminogen activator (tPA) in a final concentration of 2.4 nM. (a) A representative example of TEG tracings with tPA induced fibrinolysis before and immediately after infusions of adrenaline. (b) Comparisons of the lysis AUC values t=0 vs. t=15 and t=0 vs. t=45, respectively by 1-way ANOVA, Friedman test and post hoc Dunn's Multiple Comparison Test, **p<0.01, ns: not significant.

Figure 10:
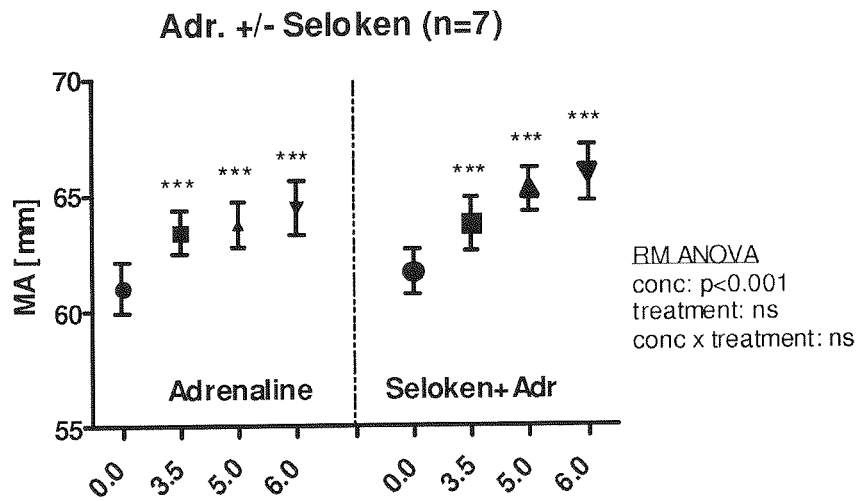
FIG. 10: Administration of adrenaline and adrenaline and seloken to 7 healthy volunteers.

FIG. 10: Seven healthy volunteers received 3 doses of adrenaline infusion lasting for 5 minutes each in the following step-wise increasing doses 3.5, 5.0 and 6.0 µg/kg/h. After resting 1 hour, the subjects received 0.15 µg/kg Seloken i.v. and rested again 30 minutes before repeating the step-wise adrenaline infusions. Blood samples were obtained from an arterial catheter at baseline (t=0.0), after each of the first adrenaline doses (t=5.0, t=10.1, t=15.0), at baseline after Seloken administration and rest (t=0.1) and after each of the subsequent adrenaline infusions (t=5.1, t=10.1, t=15.1). The blood was analyzed with TEG as described in FIG. 3 and Example 1. TEG MA values are presented as mean with 95% CI and analyzed with a 2-way repeated measurements (RM) ANOVA with post hoc Bonferroni adjusted paired t-test of t=0.0 vs. t=5.0, t=10.1, t=15.0, respectively and t=0.1 vs. t=5.1, t=10.1, t=15.1, ***p<0.001.

FIG. 11: The healthy subjects described in FIG. 10 were monitored haemodynamically at the same time points as described in FIG. 10. (a) heart rate (HR), (b) cardiac output (CO), (c) stroke volume (SV), (d) invasive blood pressure: mean arterial pressure, MAP) and (d) total peripheral resistance (TPR). All results are presented as mean with 95% CI and analyzed with 2-way repeated measurements ANOVA (RM ANOVA) followed by post hoc Bonferroni adjusted paired t-tests comparing baseline to each of the adrenaline concentrations for both treatments (without or with Seloken pre-treatment, respectively). P-values for adrenaline concentration, treatment and conc x treatment effects in the repeated measures model are shown. The conc x treatment is an analysis of the total response/the total pattern, to check whether there is an interaction between concentration and treatment. If the only significant effect was concentration, the post hoc Bonferroni results in respect of significance level are shown (a,c,d). If the effect of conc x treatment was significant ($p<0.05$), a Friedman 1-way ANOVA was performed for each treatment, followed by a Bonferroni-adjusted paired t-test comparing adrenaline concentrations separately (b). If concentration and treatment effect were significant without a significant conc x treatment effect separate Bonferroni-adjusted paired t-tests were performed directly (e). *$p<0.05$, $p<0.01$, *$p<0.001$, ns: non significant. ANOVA: Analysis of variance.

Figure 12:
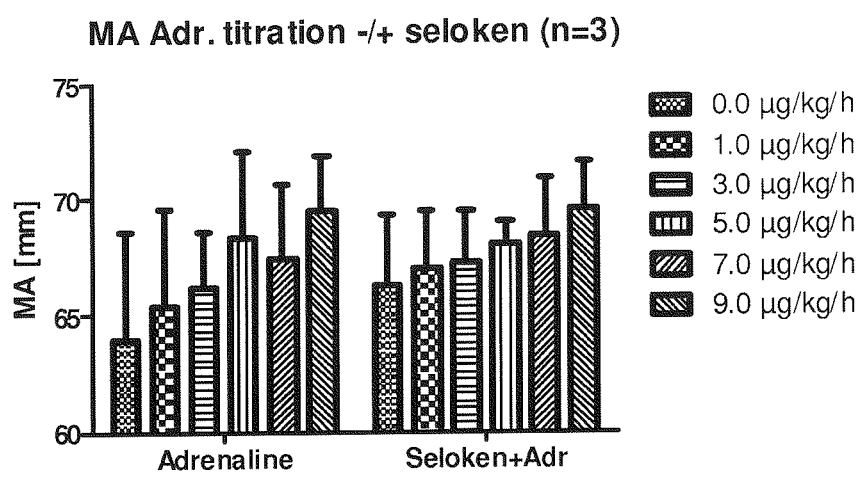
FIG. 12 shows three healthy volunteers received 5 doses of adrenaline infusion lasting for 5 minutes each in the following step-wise increasing doses 1, 3, 5, 7, and 9 µg/kg/h. After resting 1 hour, the subjects received Seloken i.v. 0.20 µg/kg for 10 minutes and rested again 30 minutes before repeating the step-wise adrenaline infusions. Blood samples were obtained from an arterial catheter at baseline (0.0 µg/kg/h)), after each of the first adrenaline doses, at baseline after Seloken administration and rest and after each of the subsequent adrenaline infusions. The blood was analyzed with TEG as described in FIG. 3 and Example 1. TEG MA values are presented as mean with 95% CI.

FIG. 12: Three healthy volunteers received 5 doses of adrenaline infusion lasting for 5 minutes each in the following step-wise increasing doses 1, 3, 5, 7, and 9 µg/kg/h. After resting 1 hour, the subjects received Seloken i.v. 0.20 µg/kg for 10 minutes and rested again 30 minutes before repeating the step-wise adrenaline infusions. Blood samples were obtained from an arterial catheter at baseline (0.0 µg/kg/h)), after each of the first adrenaline doses, at baseline after Seloken administration and rest and after each of the subsequent adrenaline infusions. The blood was analyzed with TEG as described in FIG. 3 and Example 1. TEG MA values are presented as mean with 95% Cl.

EXAMPLES

Example 1

Thrombelastography (TEG)

The TEG in vitro assay is suitable for determining important parameters in the hemostatic process including clot strength. The TEG system's approach to monitoring patient hemostasis is based on the premise that the end result of the hemostatic process is the clot. The clot's physical properties determine whether the patient will have normal hemostasis, or will be at increased risk for haemorrhage or thrombosis [Salooja et al. 2001].

The TEG analyzer uses a small whole blood sample in a rotating cup and a pin suspended in the blood by a torsion wire, which is monitored for motion. The torque of the rotating cup is transmitted to the immersed pin only after fibrin and/or fibrin-platelet bonding has linked the cup and pin together (FIG. 1). The strength and rate of these bonds affect the magnitude of the pin motion such that strong clots move the pin more than less strong clots. Thus, the TEG technology documents the interaction of platelets with the protein coagulation cascade from the time of placing the blood in the analyzer until initial fibrin formation, clot rate strengthening and fibrin-platelet bonding via GPIIb/IIIa, through eventual clot lysis (FIG. 2). The TEG R parameter reflects the initiation phase, reaction time, from start of coagulation until the first fibrin band is formed; the Angle ($\alpha$) represents the increase in clot strength, clot kinetics, correlating with the thrombin generation. The maximal amplitude (MA) parameter reflects maximal clot strength i.e. the maximal elastic modus of the clot. The area under the lysis curve, i.e. area under curve from MA is obtained (Lysis AUC) reflects degree of fibrinolyis.

The TEG system has been recognized as a uniquely useful tool and has been used extensively in the management of bleeding during major surgical interventions such as liver transplantations [Kang Y. 1995] and cardiovascular procedures [Shore-Lesserson et al. 1999] as well as obstetrics, trauma, neurosurgery, management of deep vein thrombosis, and the monitoring and differentiation among platelet GPIIb/IIIa antagonists [Di Benedetto 2003]. TEG-guided transfusion therapy aiming at normalizing clot strength (MA) has resulted in a reduction in the use of blood products, a reduction in the rate of re-exploration, prediction of bleeding in cardiac surgery and it is approved by the FDA for the monitoring of patients with heart assist devices. The clinical utility of the TEG rely in its reflection of thrombin generation and the resulting physical properties of the clot [Rivard et al. 2005].

A whole blood sample for TEG analysis was drawn into a tube containing citrate (9 volumes of blood into 1 volume of 0.129 M citrate; VACUTAINER system, BD Biosciences, Plymouth, UK) and rested for exactly 30 minutes before analysis: Coagulation was initiated by kaolin and re-calcified according to the instructions of the manufacturer: Citrated whole blood was added to a kaolin vial and mixed by gently inversion 5 times before transfer to the TEG cup containing calcium chloride (20 µl of 0.2 M $CaCl_2$), which was preloaded into the TEG® cup as published previously [Johansson et al. 2008]. The hemostatic process was recorded by use of a TEG® coagulation analyzer (5000 series, Haemoscope Corporation). Adrenaline was mixed with 0.9% NaCl and infused intravenously.

FIG. 3 illustrates TEG profiles from a representative volunteer before and after receiving intravenous infusion of adrenaline 3 µg/kg/h for 15 minutes. As illustrated in FIG. 3 and FIG. 4, the infusion of adrenaline results in a faster initiation of the coagulation process (R shorter), increased amplification and propagation of the coagulation process, i.e. increased thrombin generation (Angle increased) and a clot with an increased mechanical strength (MA increased).

Example 2

We have identified a pro-hemostatic effect of administration of sympathicomimetics, as exemplified by adrenaline infusion in 30 healthy subjects (FIGS. 3 and 4), patients prior to surgery (FIG. 7), as well as after noradrenaline administration in 10 healthy subjects (FIG. 5).

We have found a dose dependent increase in the pro-hemostatic effect of administration of sympathicomimetics where a dose of 1 microgram/kg/hour resulted in a smaller change as compared to baseline than 2 microgram/kg/hour did and the pro-hemostatic effect was further improved when 3 microgram/kg/hour was administered (FIG. 7). A dose-dependent increase in MA response was additionally observed in a series of adrenaline infusion in the doses 3.5, 5.0, 6.0 µg/kg/h (FIG. 4c).

Example 3

The Effect of Administration of Adrenaline by Intravenous Infusion on TEG Parameters in 10 Consecutive Patients Undergoing Prostatectomy Patients undergoing prostatectomy were anaesthetized by propofol and haldid. Prior to skin incision the patients received a step-wise i.v. infusion of adrenaline in the doses 1, 2 and 3 µg/kg/h each for 5 minutes. TEG analyses were performed as described in example 1, exactly 30 minutes after collection of arterial blood. Blood samples were obtained before and after each dose and 1 hour after discontinuation of adrenaline infusion. As illustrated in FIG. 7a-c administration of adrenaline result in a significantly faster initiation of the coagulations process (R decreased), increased rate of amplification and increased rate of propagation and thrombin generation (increased Angle) and an increased mechanical strength of the clot (increased MA). Furthermore, the pro-hemostatic effect of adrenaline on clot strength (MA) is abated 60 min after discontinuation of infusion. Importantly, as opposed to other pro-hemostatic therapies such as coagulation factor concentrates, activated coagulation factor concentrates and activated recombinant factor VIIa, sympathicomimetics improve clot strength (MA increase) also in humans with a normal hemostatic system, whereas conventional pro-hemostatics only improve the initiation phase (R) and thrombin generation (Angle).

Example 4

The Effect of Administration of Adrenaline by Intravenous Infusion on Perioperative Blood Loss In addition to the enhanced hemostatic response, intravenous administration of adrenaline resulted in a significant reduction in perioperative blood loss. Blood loss of the 10 patients described in example 2 and 10 additional prostatectomy patients receiving a 15 minutes continuous adrenaline infusion of 3 µg/kg/h before skin incision were compared to 40 control patients, not receiving adrenaline, whereof 20 were operated before the interventions and the last 20 subsequently after the intervention (FIG. 8). Intravenous administration of adrenaline reduced perioperative blood loss significantly.

Example 5

Safety

The pro-hemostatic effect of sympathicomimetics resulting in increased clot strength as evaluated by TEG MA could potentially increase the risk of thrombembolic events in the patients. It has previously been shown that an increase in MA after surgery is associated with increased incidence of thrombembolic complications (McCrath et al. 2005). As can be seen in the FIGS. 6 and 7c and in Example 2, the MA returns to baseline within 30 or 60 minutes, respectively, after discontinuation of adrenaline infusion and, hence, no risk for development of thrombembolic events due to increased clot strength can be anticipated after discontinuation of the drug.

Example 6

Fibrinolysis Resistance

When challenging the clot in vitro by induction of fibrinolyis, the Lysis AUC obtained by TEG (see FIG. 2) is a measure of the clot's resistance against fibrinolysis. Healthy subject received step-wise adrenaline infusion as described in FIG. 4, and blood was collected before (t=0), immediately after the infusion (t=15) and 30 minutes after discontinuation (t=45). Citrated whole blood was analysed precisely 30 minutes after blood collection: The fibrinolysis activator tPA (American Diagnostica) was added in a final concentration of 2.4 nM and TEG was performed as described in Example 1 and FIG. 3. As shown in FIG. 9, adrenaline improves the resistance against fibrinolysis by increasing the Lysis AUC significantly (154%). This effect was abrogated 30 minutes after discontinuation of adrenaline infusion. This clot stabilizing effect described above has not been observed when administering coagulation factors concentrates (activated or non-activated) or recombinant factor VIIa.

Example 7

TEG Ma in Relation to Combination of Adrenergic Receptor Agonist and Antagonists An antagonist directed at the known adrenergic receptors could potentially abrogate the sympathicomimetic induced pro-hemostatic effect as evaluated by TEG MA. Healthy volunteers rested 1 hour before receiving step-wise i.v. administration of adrenaline in the doses 3.5, 5.0 and 6.0 µg/kg/h, five minutes infusion at each dose, as described in FIG. 4. Hereafter the subjects rested for 1 hour and received an antagonist by i.v. infusion propanolol (primarily a β-2 antagonist, 0.15 mg/kg for 10 minutes), n=8, Urapidil (α-1 antagonist, 50 mg) or Seloken (β-1 antagonist 0.15 mg/kg for 10 minutes), n=7. The subjects rested another 30 minutes after receiving antagonist and the adrenaline administration was repeated as described above. As a control, subjects also received repeated adrenaline administration without antagonist (n=6). Blood samples were collected from an arterial catheter at baseline before adrenaline (0.0) and after each dosing (3.5, 5.0, 6.0) at both adrenaline infusions. FIG. 10 illustrates that MA increases after adrenaline administration and that this response was not affected by β-1 blocking (Seloken). None of the other antagonists tested abrogated the MA increase after adrenaline infusion and showed a similar response as depicted for Seloken (FIG. 10).

Example 8

Hemodynamic Effects in Relation to Administration of a Combination of Adrenergic Receptor Agonist and Antagonists Adrenaline affects the heart and hemodynamic system, primarily through the 13-1 receptors. In connection with surgery an increased stress response is seen due to pain, intubation etc. leading to tachycardia and an increased risk of arrhythmias during surgical procedures. Additional anesthetics and/or pain relief and/or β-receptor blocking agents are used to reduce these side effects.

Figure 11A:
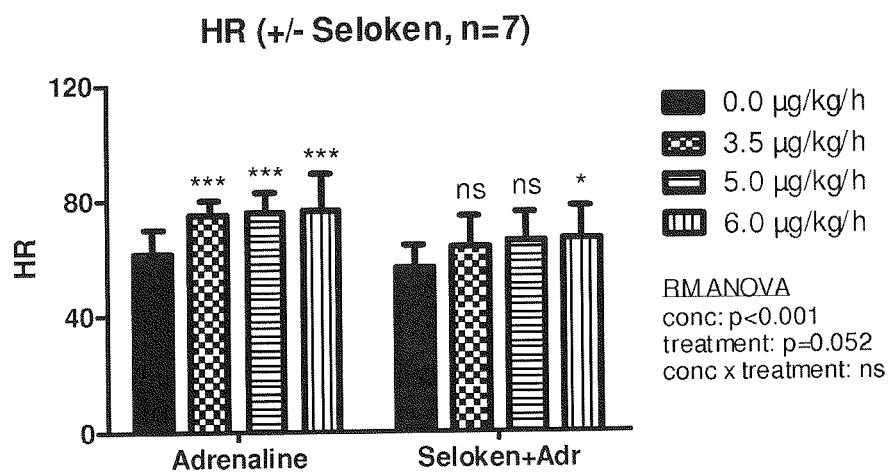
FIGS. 11 a, b, c, d, and e: The volunteers of FIG. 10 were monitored haemodynamically at the same time points as described in FIG. 10: (11a) heart rate (HR), (11b) cardiac output (CO), (11c) stroke volume (SV), (11d) invasive blood pressure: mean arterial pressure, MAP) and (11e) total peripheral resistance (TPR).
Figure 11B:
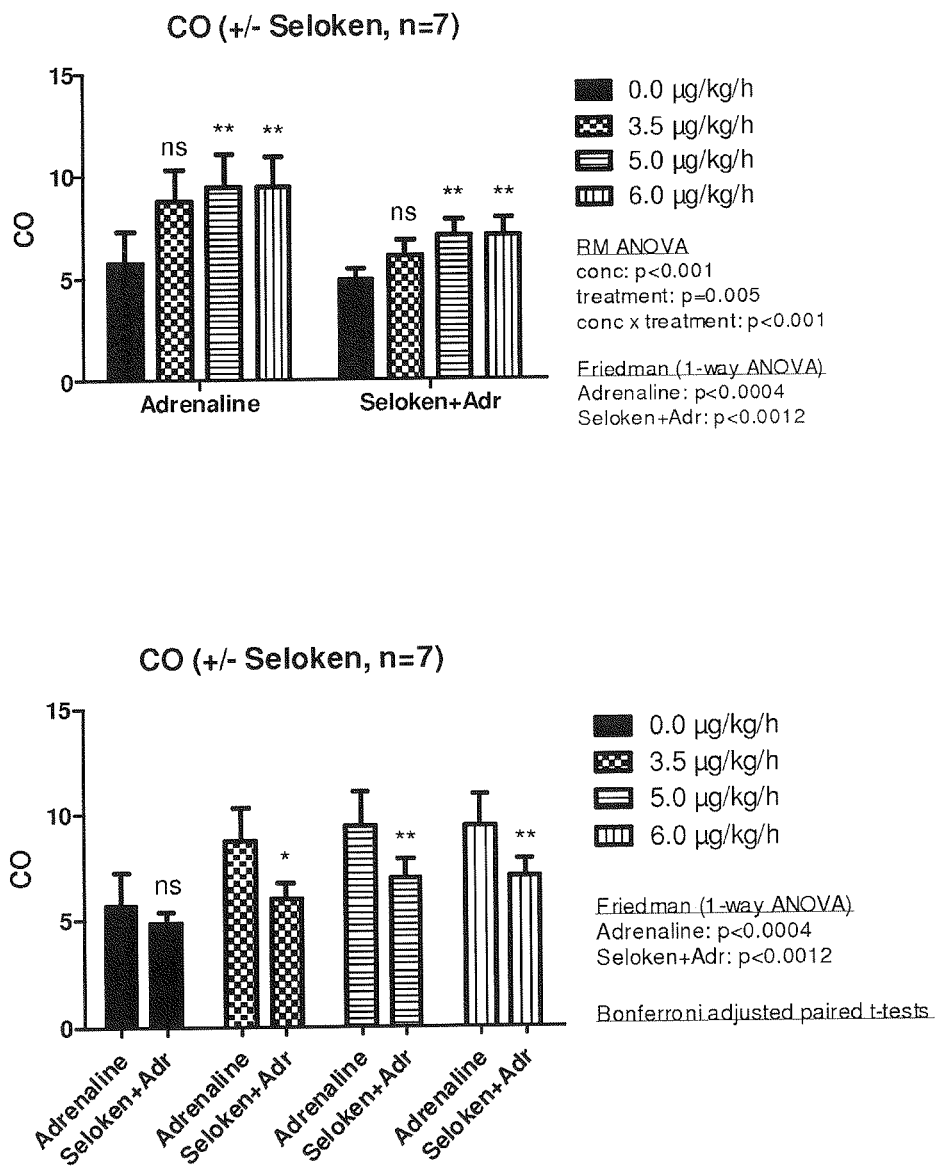
Figure 11C:
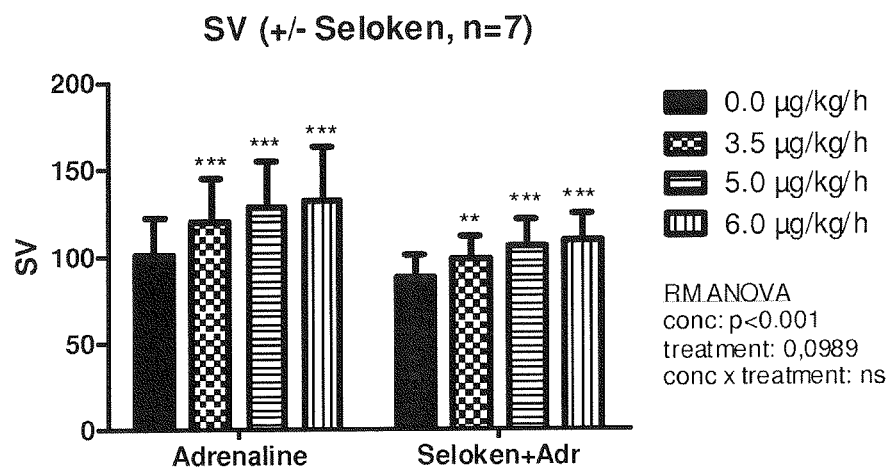
Figure 11D:
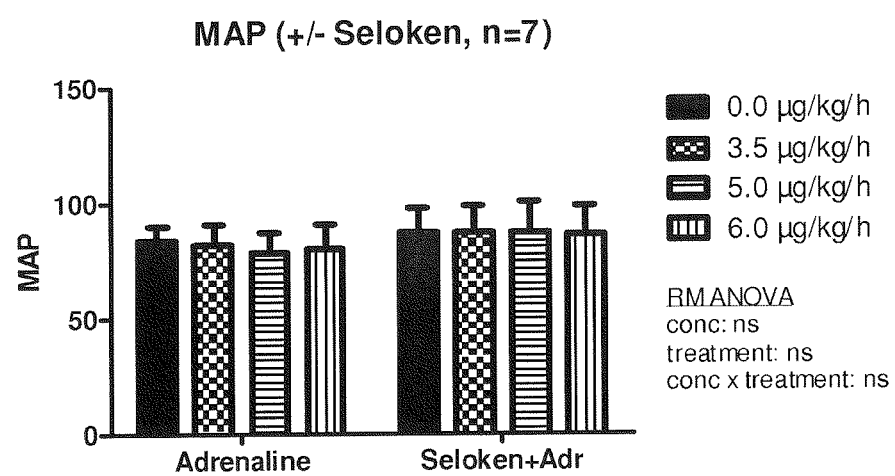
Figure 11E:
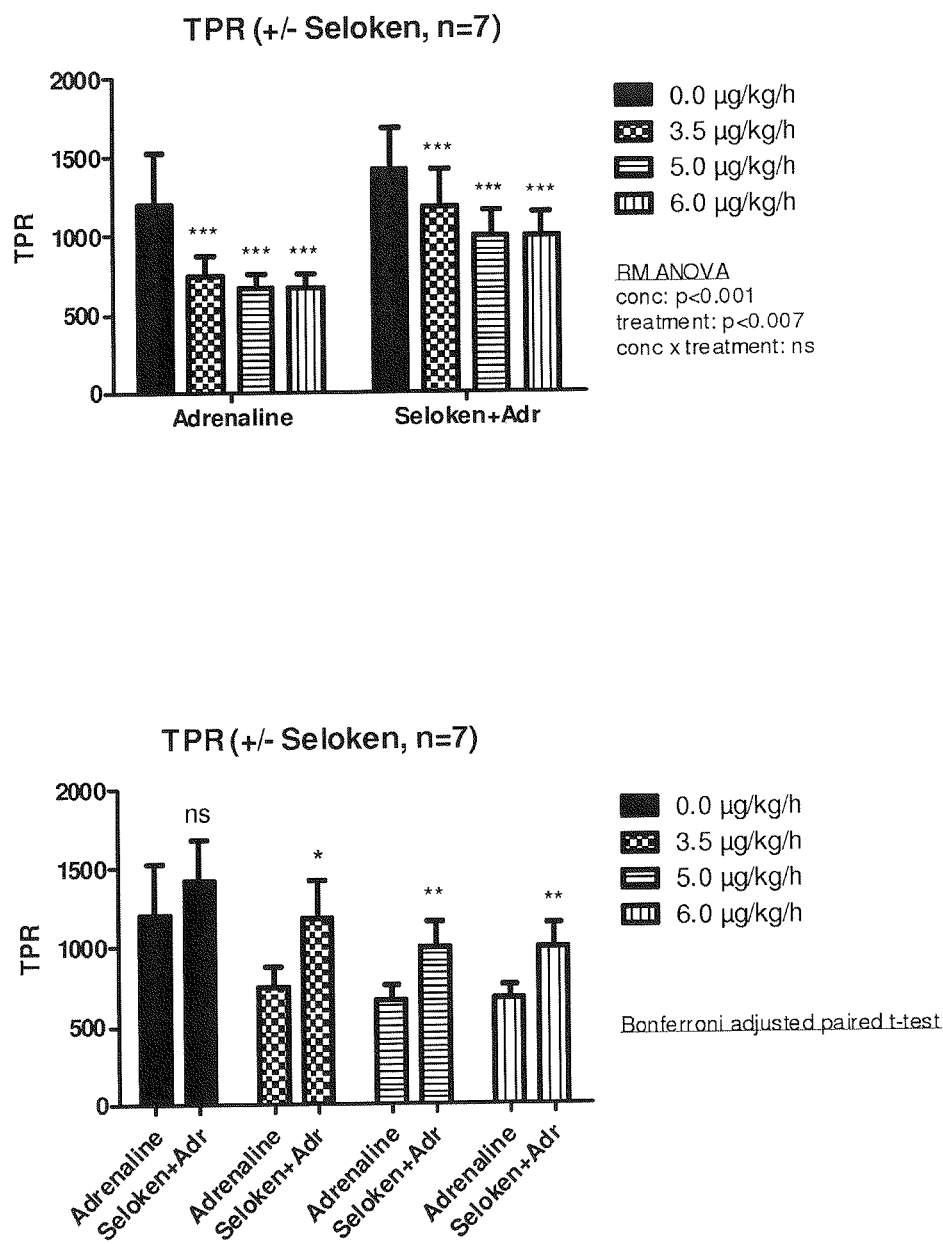

The hemodynamic changes comprising heart rate (HR), cardiac output (CO), stroke volume (SV), mean arterial pressure (MAP) and total peripheral resistance (TPR) were monitored during the protocol described in example 7 and FIG. 10. FIG. 11 depict the hemodynamic changes in response to adrenaline before and after administration of the (β-1 receptor antagonist Seloken. Adrenaline alone increased HR significantly, whereas this effect was practically abrogated/normalized when Seloken was infused (FIG. 11a) and as the effect of treatment nearly showed significance (p<0.052) post hoc separate Bonferroni adjusted paired t-test was completed showing significant differences in HR at the adrenaline doses 5.0 and 6.0 before and after Seloken. The increase in CO in response to adrenaline infusions (FIG. 11b) was significantly lower in all adrenaline concentrations when Seloken was administered. The increase in SV (FIG. 11c) was not significantly lowered after Seloken administration and no effects on the MAP were detected at any of the adrenaline doses used in the described protocol (FIG. 11d). A significant decrease in TPR was observed for all adrenaline doses both with and without Seloken with a significant effect of Seloken. Separate Bonferroni adjusted t-tests showed a significantly lower decrease in adrenaline response after Seloken treatment (FIG. 11e).

In conclusion, infusion of a β-1 receptor blocker almost normalizes the increase in HR, reduces the increase in CO and reduces the decrease in TPR, seen in response to adrenaline infusion.

Example 9

Three healthy volunteers received 5 doses of adrenaline infusion lasting for 5 minutes each in the following step-wise increasing doses 1, 3, 5, 7, and 9 μg/kg/h. After resting 1 hour, the subjects received Seloken i.v. 0.20 μg/kg for 10 minutes and rested again 30 minutes before repeating the step-wise adrenaline infusions. Blood samples were obtained from an arterial catheter at baseline (0.0 μg/kg/h)), after each of the first adrenaline doses, at baseline after Seloken administration and rest and after each of the subsequent adrenaline infusions. The blood was analyzed with TEG as described in FIG. 3 and Example 1. TEG MA values are presented as mean with 95% Cl.

Plasma K+ concentrations where followed before and after administration of both adrenaline and Seloken (beta blocker). As can be seen from Table 1, the plasma potassium concentrations fell following adrenaline administration. The drop in plasma potassium concentration was less when Seloken was administered prior to the administration of adrenaline.

TABLE 1

Plasma concentration of $K^+$: Plasma potassium ($K^+$) was measured in the healthy subjects described in FIG. 12 before and after adrenaline infusion with 9.0 μg/kg/h before and after Seloken administration.

| Person | Before Seloken Baseline | Before Seloken After adrenaline | After Seloken Baseline | After Seloken After adrenaline |
|---|---|---|---|---|
| 1 | 4.1 | 3.2 | 4.0 | 3.7 |
| 2 | 3.9 | 3.3 | 4.1 | 3.7 |
| 3 | 4.0 | 3.2 | 3.9 | 3.7 |

REFERENCES

Roberts H R, Hoffman M, Monroe D M. A cell-based model of thrombin generation. Semin Thromb Hemost. 2006 April; 32 Suppl 1:32-8.

Singh M, Singh P, Kaur H. Plasma protein variations in hemophiliacs receiving factor replacement therapy. Indian J. Pediatr. 2007 May; 74(5):459-62.

Brace L D. Qualitative platelet disorders. Clin Lab Sci. 2007 Winter; 20(1):48-55.

Vaslev S N, Knudsen N R, Neligan P J, Sebastian M W. Massive transfusion exceeding 50 units of blood products in trauma patients. J Trauma 2002; 53:291-296

Hardy J F, de Moerloose P, Samama C M. The coagulopathy of massive transfusion. Vox Sang 2005; 89(3):123-7.

Cheung A T, To P L, Chan D M, Ramanujam S, Barbosa M A, Chen P C, Driessen B, Jahr J S, Gunther R A. Comparison of treatment modalities for hemorrhagic shock. Artif Cells Blood Substit Immobil Biotechnol. 2007; 35(2):173-90.

Society of Thoracic Surgeons Blood Conservation Guideline Task Force, Ferraris V A, Ferraris S P, Saha S P, Hessel E A 2nd, Haan C K, Royston B D, Bridges C R, Higgins R S, Despotis G, Brown J R; Society of Cardiovascular Anesthesiologists Special Task Force on Blood Transfusion, Spiess B D, Shore-Lesserson L, Stafford-Smith M, Mazer C D, Bennett-Guerrero E, Hill S E, Body S. Perioperative blood transfusion and blood conservation in cardiac surgery: the Society of Thoracic Surgeons and The Society of Cardiovascular Anesthesiologists clinical practice guideline. Ann Thorac Surg. 2007 May; 83 (5 Suppl):S27-86.

Stainsby D, Jones H, Asher D, Atterbury C, Boncinelli A, Brant L, Chapman C E, Davison K, Gerrard R, Gray A, Knowles S, Love E M, Milkins C, McClelland D B, Norfolk D R, Soldan K, Taylor C, Revill J, Williamson L M, Cohen H; SHOT Steering Group. Serious hazards of transfusion: a decade of hemovigilance in the UK. Transfus Med Rev. 2006 October; 20(4):273-82.

Banbury M K, Brizzio M E, Rajeswaran J, Lytle B W, Blackstone E H. Transfusion increases the risk of postoperative infection after cardiovascular surgery. J Am Coll Surg. 2006 January; 202 (1):β1-8.

Jeschke M G, Chinkes D L, Finnerty C C, Przkora R, Pereira C T, Herndon D N. Blood transfusions are associated with increased risk for development of sepsis in severely burned pediatric patients. Crit. Care Med. 2007 February; 35(2): 579-83.

Milasiene V, Stratilatovas E, Characiejus D, Kazbariene B, Norkiene V. TGF-beta 1 and TNF-alpha after red blood cell transfusion in colorectal cancer patients. Exp Oncol. 2007 March; 29(1):67-70.

Zallen G, Offner P J, Moore E E et al. Age of transfused blood is an independent risk factor for postinjury multiple organ failure. Am J. Surg. 1999; 178:570-2.

Hebert P C, Wells G, Blajchman M A, Marshall J, Martin C, Pagliarello G, Tweeddale M, Schweitzer I, Yetisir E. A multicenter, randomized, controlled clinical trial of transfusion requirements in critical care. Transfusion Requirements in Critical Care Investigators, Canadian Critical Care Trials Group. N Engl J. Med. 1999 February 11; 340(6):409-17.

Engoren M C, Habib R H, Zacharias A, Schwann T A, Riordan C J, Durham S J. Effect of blood transfusion on long-term survival after cardiac operation. Ann Thorac Surg. 2002 October; 74(4):1180-6.

Karkouti K, Wijeysundera D N, Yau T M, Beattie W S, Abdelnaem E, McCluskey S A, Ghannam M, Yeo E, Djaiani G, Karski J. The independent association of massive blood loss with mortality in cardiac surgery. Transfusion. 2004 October; 44(10):1453-62.

Reed W, Lee T H, Norris P J, Utter G H, Busch M P. Transfusion-associated microchimerism: a new complication of blood transfusions in severely injured patients. Semin Hematol. 2007 January; 44(1):24-31.

Goldstein D S. Adrenaline and the inner world. Johns Hopkins university Press 2006.

Cannon W B, Mendenhall W L. Factors influencing the coagulation of blood. IV The hastening of blood coagulation in pain and emotional excitement. Am J Physiol 1914; 34:251-261.

Colman R W, Clowes A W, George J N, Hirsh J, Marder V J (eds). Hemostasis and Thrombosis. Basic principles and clinical practice. Philadelphia, Williams & Wilkins 2001.

Smith J E: Effects of strenuous exercise on hemostasis. Br J Sports Med 2003; 37:433-435.

el-Sayed M S: Effects of exercise on blood coagulation, fibrinolysis and platelet aggregation. Sports Med 1996; 22:282-298.

Teppo H, Virkkunen H, Revonta M. Topical adrenaline in the control of intraoperative bleeding in adenoidectomy: a randomised, controlled trial. Clin Otolaryngol. 2006 August; 31(4):303-9.

Johansson P I. The Blood Bank: From Provider to Partner in Treatment of Massively Bleeding Patients. Transfusion 2007; 47:176 S-181S.

Welsby I J, Jiao K, Ortel T L, Brudney C S, Roche A M, Bennett-Guerrero E, Gan T J. The kaolin-activated Thrombelastograph predicts bleeding after cardiac surgery. J Cardiothorac Vasc Anesth. 2006; 20:531-5

Salooja N, Perry D J. Thrombelastography. Blood Coagul Fibrinolysis 2001 July; 12(5):327-37.

Kang Y. Thromboelastography in liver transplantation. Semin Thromb Hemost 1995; 21 Suppl 4:34 44.

Shore-Lesserson L, Manspeizer H E, DePerio M, Francis S, Vela-Cantos F, Ergin M A. Thromboelastography-guided transfusion algorithm reduces transfusions in complex cardiac surgery. Anesth Analg 1999 February; 88(2):312-9.

Rivard G E, Brummel-Ziedins K E, Mann K G, Fan L, Hofer A, Cohen E. Evaluation of the profile of thrombin generation during the process of whole blood clotting as assessed by thrombelastography. J Thromb Haemost. 2005 September; 3(9):2039-43.

Kawasaki J, Katori N, Kodaka M, Miyao H, Tanaka K A. Electron microscopic evaluations of clot morphology during thrombelastography. Anesth Analg. 2004 November; 99(5):1440-4;

Fries D, Haas T, Klingler A, Streif W, Klima G, Martini J, Wagner-Berger H, Innerhofer P. Efficacy of fibrinogen and prothrombin complex concentrate used to reverse dilutional coagulopathy—a porcine model. Br J. Anaesth. 2006 October; 97(4):460-7.

Martini W Z. The effects of hypothermia on fibrinogen metabolism and coagulation function in swine. Metabolism. 2007 February; 56(2):214-21.

Bassus S, Wegert W, Krause M, Escuriola-Ettinghausen C, Siegemund A, Petros S, Scholz T, Scharrer I, Kreuz W, Engelmann L, Kirchmaier C M. Platelet-dependent coagulation assays for factor VIII efficacy measurement after substitution therapy in patients with haemophilia A. Platelets. 2006 September; 17(6):378-84.

Gottumukkala V N, Sharma S K, Philip J. Assessing platelet and fibrinogen contribution to clot strength using modified thromboelastography in pregnant women. Anesth Analg. 1999 December; 89(6):1453-5.

Velik-Salchner C, Haas T, Innerhofer P, Streif W, Nussbaumer W, Klingler A, Klima G, Martinowitz U, Fries D. The effect of fibrinogen concentrate on thrombocytopenia. J Thromb Haemost. 2007 May; 5(5):1019-25

Niemi T T, Suojaranta-Ylinen R T, Kukkonen S I, Kuitunen A H. Gelatin and hydroxyethyl starch, but not albumin, impair hemostasis after cardiac surgery. Anesth Analg. 2006 April; 102(4):998-1006.

Sorensen B, Ingerslev J. Tailoring hemostatic treatment to patient requirements—an update on monitoring hemostatic response using thrombelastography. Haemophilia. 2005 November; 11 Suppl 1:1-6

Tomokiyo K, Nakatomi Y, Araki T, Teshima K, Nakano H, Nakagaki T, Miyamoto S, Funatsu A, Iwanaga S. A novel therapeutic approach combining human plasma-derived Factors VIIa and X for haemophiliacs with inhibitors: evidence of a higher thrombin generation rate in vitro and more sustained hemostatic activity in vivo than obtained with Factor VIIa alone. Vox Sang. 2003 November; 85(4): 290-9.

McCrath D J, Cerboni E, Frumento R J, Hirsh A L, Bennett-Guerrero E. Thromboelastography maximum amplitude predicts postoperative thrombotic complications including myocardial infarction. Anesth Analg. 2005; 100:1576-83.

The invention claimed is:

1. A method for treatment of bleeding, comprising intravenous administration of an effective amount of an adrenergic receptor agonist selected from the group consisting of adrenaline and noradrenaline to a human resulting in a systemic concentration of the agonist, wherein said human has normal clot strength and stability, and wherein the agonist is administered continuously.

2. The method of claim 1, wherein the effective amount is a dose of the agonist administered in the range 0.1 to 100 microgram/kg.

3. The method of claim 1, wherein the effective amount is a dose of the agonist in the range 0.1 microgram/kg/hour to 25 microgram/kg/hour.

4. The method of claim 1, wherein the effective amount is a dose of the agonist in the range of 1 to 20 microgram/kg/hour.

* * * * *